United States Patent
Fonte

(10) Patent No.: US 9,283,006 B2
(45) Date of Patent: Mar. 15, 2016

(54) OSTEOSYNTHETIC SHAPE MEMORY MATERIAL INTRAMEDULLARY BONE STENT AND METHOD FOR TREATING A BONE FRACTURE USING THE SAME

(71) Applicant: MX Orthopedics, Corp., Billerica, MA (US)

(72) Inventor: Matthew Fonte, Concord, MA (US)

(73) Assignee: MX Orthopedics, Corp., Billerica, MA (US)

( * ) Notice: Subject to any disclaimer, the term of this patent is extended or adjusted under 35 U.S.C. 154(b) by 173 days.

(21) Appl. No.: 13/624,643

(22) Filed: Sep. 21, 2012

(65) Prior Publication Data
US 2013/0123785 A1    May 16, 2013

Related U.S. Application Data

(60) Provisional application No. 61/537,766, filed on Sep. 22, 2011, provisional application No. 61/570,091, filed on Dec. 13, 2011.

(51) Int. Cl.
*A61B 17/56* (2006.01)
*A61B 17/72* (2006.01)
*A61B 17/00* (2006.01)

(52) U.S. Cl.
CPC .............. *A61B 17/72* (2013.01); *A61B 17/7216* (2013.01); *A61B 17/7225* (2013.01); *A61B 2017/00867* (2013.01)

(58) Field of Classification Search
CPC .................... A61B 17/7275; A61B 17/7225
USPC ...................................................... 606/62–68
See application file for complete search history.

(56) References Cited

U.S. PATENT DOCUMENTS

| | | |
|---|---|---|
| 3,710,789 A | 1/1973 | Ersek |
| 4,503,569 A | 3/1985 | Dotter |
| 4,512,338 A | 4/1985 | Balko et al. |
| 4,627,434 A | 12/1986 | Murray |
| 4,733,665 A | 3/1988 | Palmaz |

(Continued)

FOREIGN PATENT DOCUMENTS

EP      0819413      1/1998

OTHER PUBLICATIONS

Duerig et al., Overview of Superelastic Stent Design, Min Invas Ther & Allied Technol, 2000, pp. 235-246, 9(3/4).

(Continued)

*Primary Examiner* — Ellen C Hammond
*Assistant Examiner* — Stuart S Bray
(74) *Attorney, Agent, or Firm* — Pandiscio & Pandiscio

(57) ABSTRACT

A method for providing stabilization and compression of a bone fracture, the method comprising: providing an intramedullary prosthesis sized for insertion into the intramedullary canal of a bone and having a distal end, a proximal end and a porous structure therebetween, wherein (i) in a first state, the prosthesis is longitudinally expanded and radially contracted, and (ii) in a second state, the prosthesis is longitudinally contracted and radially expanded, conforms to the shape of the adjacent bone and exerts forces on the adjacent bone; and positioning the intramedullary prosthesis within the intramedullary canal of a bone so that the intramedullary prosthesis spans the bone fracture, whereby to provide stabilization and compression of the bone fracture.

21 Claims, 28 Drawing Sheets

NITI STENT WITH INTEGRAL BARBS FOR GRAPPLING BONE TISSUE

(56) References Cited

U.S. PATENT DOCUMENTS

| | | |
|---|---|---|
| 4,922,905 A | 5/1990 | Strecker |
| 4,950,227 A | 8/1990 | Savin et al. |
| 4,969,888 A | 11/1990 | Scholten et al. |
| 5,061,275 A | 10/1991 | Wallsten et al. |
| 5,089,006 A | 2/1992 | Stiles |
| 6,127,597 A | 10/2000 | Beyar et al. |
| 6,761,731 B2 | 7/2004 | Majercak |
| 7,947,135 B2 | 5/2011 | Fonte |
| 7,985,222 B2 | 7/2011 | Gall et al. |
| 8,062,378 B2 | 11/2011 | Fonte |
| 2002/0032444 A1 | 3/2002 | Mische |
| 2005/0240190 A1 | 10/2005 | Gall et al. |
| 2008/0177262 A1 | 7/2008 | Augoyard et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269808 A1 | 10/2008 | Gall et al. |
| 2010/0241120 A1 | 9/2010 | Bledsoe et al. |
| 2011/0004212 A1 | 1/2011 | Gall et al. |

OTHER PUBLICATIONS

Stoeckel et al., a Survey of Stent Designs, Min Invas Ther & Allied Technol, 2002, pp. 137-147, 11(4).

ASTM International, Standard Specification and Test Methods for Intramedullary Fixation Devices, 2007.

Bong et al., Intramedullary Nailing of the Lower Extremity: Biomechanics and Biology, Journal of the American Academy of Orthopaedic Surgeons, vol. 15, No. 2, Feb. 2007, pp. 97-106.

Kuala et al, Bone modeling controlled by a nickel-titanium shape memory alloy intramedullary nail: Biomaterials 23, 2002, pp. 2535-2543.

Synthes, Synthes Titanium intramedullary Nails Comprehensive Product Range, Original instuments and implants of the Association for the Study of Internal Fixation—AO ASIF, 2003.

CP Stent™ Foreshortening Chart

| INFLATED BALLOON DIAMETER | CP8Z16 (LENGTH AFTER EXPANS.) (% shortening) | CP8Z22 (LENGTH AFTER EXPANS.) (% shortening) | CP8Z28 (LENGTH AFTER EXPANS.) (% shortening) | CP8Z34 (LENGTH AFTER EXPANS.) (% shortening) | CP8Z39 (LENGTH AFTER EXPANS.) (% shortening) | CP8Z45 (LENGTH AFTER EXPANS.) (% shortening) |
|---|---|---|---|---|---|---|
| 12mm | 1.61cm (2.8%) | 2.18cm (0.8%) | 2.62cm (4.4%) | 3.23cm (3.1%) | 3.72cm (1.9%) | 4.17cm (3.8%) |
| 14mm | 1.54cm (6.5%) | 2.08cm (5.4%) | 2.56cm (6.8%) | 3.15cm (5.4%) | 3.66cm (3.6%) | 3.97cm (8.4%) |
| 15mm | 1.51cm (8.5%) | 2.02cm (7.9%) | 2.51cm (8.8%) | 3.10cm (7.0%) | 3.54cm (6.6%) | 3.94cm (9.2%) |
| 16mm | 1.48cm (10.6%) | 1.98cm (10.1%) | 2.45cm (10.7%) | 3.00cm (9.8%) | 3.48cm (8.2%) | 3.84cm (11.4%) |
| 18mm | 1.43cm (13.7%) | 1.89cm (14.0%) | 2.38cm (13.3%) | 2.88cm (13.5%) | 3.20cm (15.6%) | 3.71cm (14.5%) |
| 20mm | 1.32cm (20.0%) | 1.80cm (17.9%) | 2.30cm (16.3%) | 2.63cm (20.9%) | 2.96cm (21.9%) | 3.27cm (24.7%) |
| 22mm | 1.23cm (25.4%) | 1.67cm (23.9%) | 2.09cm (24.0%) | 2.46cm (26.0%) | 2.85cm (25.0%) | 3.15cm (27.3%) |
| 24mm | 1.05cm (36.4%) | 1.46cm (33.8%) | 1.91cm (30.3%) | 2.07cm (37.9%) | 2.27cm (40.1%) | 2.83m (34.9%) |

NITINOL STENT IN THE COLLAPSED STATE PRE-INSERTION AND IN THE EXPANDED STATE. NOTICE THE LARGE LENGTH CHANGE DURING EXPANSION.

FIG. 14

E, GPA IS THE MEASURE OF THE MATERIAL'S STIFFNESS OR MODULUS OF ELASTICITY.

$$F = \frac{Etw^3}{L^3} \cdot \delta$$

$$\varepsilon = \frac{3w}{L^2} \cdot \delta$$

Solve for STRAIN and FORCE $$Strain = \varepsilon = \frac{3w}{L^2} \cdot \delta$$

$$Force = F = \frac{12EI}{L^3} \cdot \delta$$

$E$ = modulus of elasticity
$I$ = moment of inertia, beam cross section
$w$ = Strut Width
$L$ = strut length

NITI STENT WITH INTEGRAL BARBS FOR GRAPPLING BONE TISSUE

MEDULLARY CANAL

OSTEOSYNTHETIC SHAPE MEMORY MATERIAL INTRAMEDULLARY BONE STENT AND METHOD FOR TREATING A BONE FRACTURE USING THE SAME

REFERENCE TO PENDING PRIOR PATENT APPLICATIONS

This patent application claims benefit of:

(i) pending prior U.S. Provisional Patent Application Ser. No. 61/537,766, filed Sep. 22, 2011 by Matthew Fonte for OSTEOSYNTHETIC SHAPE MEMORY MATERIAL INTRAMEDULLARY BONE STENTS AND METHODS FOR TREATING BONE FRACTURES USING THE SAME; and (ii) pending prior U.S. Provisional Patent Application Ser. No. 61/570,091, filed Dec. 13, 2011 by Matthew Fonte for OSTEOSYNTHETIC SHAPE MEMORY MATERIAL INTRAMEDULLARY BONE STENTS AND METHODS FOR TREATING BONE FRACTURES USING THE SAME.

The two (2) above-identified patent applications are hereby incorporated herein by reference.

BACKGROUND OF THE INVENTION

Introduction: Osteosynthesis is the reduction and fixation of a bone fracture with an implantable device. The device is usually made of metal, either titanium or stainless steel, and may include plates, pins, rods, screws, and staples. It is a surgical procedure with an open or percutaneous approach to the fractured bone. The procedure aims to bring the fractured bone segments together and immobilize the fracture site while healing takes place. The use of osteosynthetic devices has a long history and a reasonable record of success.

Bone Fractures: A bone fracture is a medical condition in which there is a break in the continuity of the bone. A fracture may result from either a high impact force or a low impact force, frequently as a result of a medical condition that weakens the bone, such as osteoporosis. Bone fractures can be complete or incomplete, simple or comminuted, closed or open. Comminuted fractures comprise more than two bone fragments, and open fractures are associated with an open skin wound. While many fractures are treated non-operatively, a large number of fractures require surgical intervention. If a fracture that requires operative treatment is not treated, nature tries to stabilize the mobile fragments by pain-induced contraction of the surrounding muscles, which may lead to bone shortening. The end result of this process frequently is the lack of proper bone alignment and impaired function.

For lower extremity fractures, stability for weight bearing is the main goal. In the upper extremity, restoration of functional hand and arm motion is most important. For diaphyseal fractures, proper alignment of the fracture fragments is typically all that is needed for adequate function and prompt healing of the fracture, whereas intraarticular fractures require precise anatomic reduction with articular congruency being very important.

Fracture Fixation: The basic goal of fracture fixation is to stabilize the fractured bone, to enable fast healing of the injured bone, and to return mobility and function of the injured extremity. This is accomplished either by using conservative treatment methods (non-surgical) or by using mechanical fixation devices (surgical). Mechanical fixation devices may either be external to the body (i.e., ring fixation), or internal to the body (i.e., rods, pins, and plates).

There are two types of fixation, flexible (biologic) and rigid. With flexible fixation, the fracture fragments displace in relation to each other when load is applied across the fracture site. Fracture fixation is considered flexible if it allows appreciable interfragmentary movement under functional load. Fracture healing under flexible fixation typically occurs by means of callus formation.

Rigid fixation provides immobilization and allows fractures to heal by the process of intramembranous ossification. Rigid fracture fixation is desirable for fractures that involve articulating surfaces. Bridging of the fracture with a stiff splint reduces mobility of the fracture fragments and allows minimal displacement under functional load. Articular fractures require exact anatomic reduction and stable fixation to avoid development of abundant callus. This is important because unevenness of the joint surface and presence of callus formation at the articular surface lead to patient discomfort and often development of early and progressive osteoarthritis.

The only technique that effectively abolishes motion at the fracture site is interfragmentary compression which uses a plate and screws to completely eliminate motion at the fracture site, and allows for direct healing without formation of visible callus. However, in some cases, over time, the stainless steel and titanium fixation devices do not maintain compression across the fracture fragments. The reduction of compression has been observed to be as much as 32% over a two week period. Additionally, as the necrotic surfaces of the fracture are resorbed, a non-load bearing gap develops between the fragments, thereby decreasing compression and increasing the risk of interfragmentary motion and scar tissue formation.

Loss of compression is contrary to the objectives of fracture fixation in general. Excessive interfragmentary motion results in the formation of fibrous, unmineralized scar tissue (resulting in a non-union or pseudoarthrosis) versus the regeneration of bone. The unmineralized scar tissue does not support load and may lead to loss of skeletal function. In addition to compression across the fracture site, a sufficient blood supply must be maintained to support skeletal metabolism, bone regeneration, and remodeling of the fracture site.

Conservative Fracture Treatment: Conservative treatment utilizes non-surgical methods to restore the alignment and subsequent stabilization of the affected bones. Conservative treatment is achieved by traction or by external splinting. Traction devices are temporarily applied along the long axis of the bone, to align the bone fragments and provide some stability. See FIG. 1, which shows a simple traction device.

External Fixation: External fixators provide fracture fixation based on the principle of splinting. They are the only systems that allow the surgeon to control the flexibility of the fixation system. External fixators are the standard in treating open fractures that present with substantial soft-tissue injuries and require additional vascular procedures, fasciotomy, soft-tissue flaps, or multiple debridements, to avoid additional damage to an already compromised limb. Additionally, external fixation may be indicated for polytrauma, fractures in children to avoid pin fixation through the growth plate, temporary joint bridging before later open reduction internal fixation (ORIF), and arthrodesis of the ankle, elbow, or knee. In these latter cases, external fixators are especially indicated in acute or chronic infections, in limb-lengthening procedures, and occasionally after corrective osteotomies.

External fixators are made of pins or wires (Schanz screws, Steinman pins, Kirschner wires) that are placed percutaneously into the bone above and below the fracture site. These pins or wires are connected by various clamps to external fixation rods (stainless steel or carbon fiber rods). There are two basic types of external fixators: standard pin fixator ring and hybrid fixator. Standard uniplanar external fixators consist of percutaneously placed pins that are connected to an external rod. Proper pin or screw placement is very important. These pins or screws should penetrate the near cortex and medullary canal and engage the far cortex without penetrating the muscle compartment. Joint penetration by any of these pins must be avoided. Standard uniplanar fixators can be used for almost every long bone fracture except those involving the proximal femur or humerus. They are commonly used for the stabilization of complex distal radius fractures. The pins are placed in the distal radius and second metacarpal shaft. This technique uses the surrounding soft tissues or ligamentotaxis to provide indirect stabilization of the fracture. See FIG. 2, which shows an external fixation device.

Internal Fixation: Since the late 1950s, open reduction internal fixation (ORIF) has been used to restore bone anatomy and enable early mobilization and to overcome the limitations encountered when fractures are treated with skeletal traction or cast immobilization. The main goal of internal fixation is the achievement of prompt and, if possible, full function of the injured limb, with rapid rehabilitation of the patient. The majority of internal fixation implants are currently made of stainless steel. Occasionally, less strong but biologically superior and more elastic titanium implants are favored. Numerous devices are available for internal fixation. These devices can be roughly divided into a few major categories: wires, pins and screws, plates, and intramedullary nails or rods. Staples and clamps are also used occasionally for osteotomy or fracture fixation.

Pins: Fixation pins can be smooth or threaded and are made in a large number of sizes. Among the most commonly used are Kirschner (K) wires and Steinman pins. These devices are used for temporary fixation of the fracture fragments during fracture reduction, and as guides for the accurate placement of larger cannulated screws. The percutaneously placed Kirschner wires commonly protrude through the skin for ease of later removal. Occasionally, the pins are used for definitive fracture treatment (skeletal stabilization) and should be watched for migration. The Steinman pin is also occasionally used for wrist arthrodesis. See FIG. 3, which shows Steinman pins.

Wires: Wires are used alone or more commonly in combination with other orthopedic fixation devices. They are of various diameters and may be braided. Wires are frequently used to re-attach osteotomized bone fragments (i.e., greater trochanter or olecranon). In combination with pins or screws, the wires are used to create a tension band, which uses muscular forces to create compression at the fracture site. Wires are used to suture bone and soft tissue, and while wires may break, if there is no loss of bone fragment position, breakage of wires is usually of little significance. Circumferential cerclage wires are commonly used in conjunction with intramedullary fixation to stabilize long bone fragments. One of the potential complications with cerclage wires is interruption of the periosteal blood supply with subsequent osteonecrosis or fracture nonunion. See FIG. 4, which shows examples of wires used in orthopedic fixation.

Screws: Screws are of different sizes and can be self-tapping (i.e., have cutting ends) or non-self-tapping (i.e., require a prepared tapped hole). Non-self-tapping screws are easier to insert and remove, but they are not the best choice for fixing fractures in regions with a thin cortex. Some screws have a "standard" point and others a "trocar" point. Screws are commonly used in combination with plates and nails or rods. The use of different types and designs of screws depends on the surgeon's preference. Screws may be cannulated (i.e., have a hollow central shaft) so that they can be accurately implanted using a guide wire.

There are two basic types of fixation screws, cortical and cancellous. Cortical screws are often fully threaded and usually have a smaller thread diameter and pitch. They are designed to be used in the diaphysis. Cancellous screws are intended to cross long segments of cancellous bone. They typically have deeper threads, larger thread diameter, and a greater pitch than cortical screws, and they are usually partially threaded, with threads only on their ends. Occasionally, cancellous screws can be fully threaded. See FIG. 5, which shows common orthopedic screws.

Loosening of well-placed screws is induced by micro motion at the interface between the thread and bone. From a radiologic standpoint, it is important to observe and report possible complications including screw breakage, loosening, or changes in position.

Plates: Plates can be used for both rigid and flexible fracture fixation. The majority of these plates are made of stainless steel or titanium. See FIG. 6, which shows an exemplary orthopedic bone plate.

The terminology that is commonly used with fracture plating is "compression plating" and "neutralization plating." Compression plating applies compression to the fracture ends. In cases of severely comminuted fractures, bone loss, or other situations that prevent compression, the plate is screwed into place to hold the fracture fragments together during healing. Frequently, not all the screw holes in the plate are filled. When diaphyseal fractures in the long bones are treated with a plate, a minimum of six cortices should preferably be engaged at each fracture site, except for the femur, which requires eight. Plates are most commonly used for fixation of long bones, but they also are used in the spine and for arthrodesis of the wrist.

The dynamic compression plate (DCP) has holes designed for axial compression, which is achieved by means of eccentric screw insertion. The DCP functions in different modes: compression, neutralization, tension band, or as a buttress. It is available in different sizes to accommodate fracture fixation in bones of different sizes. The screw holes in the DCP are oval and are best described as a portion of an inclined and angled cylinder. The plate can be used with different types of screws. From the radiologic standpoint, important considerations are the location of the plate, whether the plate symmetrically spans the fracture, and the degree of fracture reduction. The plate should not impinge on joint motion, and the plate and the screws should not violate the articular surface. A major complication with plating is the potential compromising of cortical blood supply because of the large contact area between the plate and the underlying cortex. See FIG. 7, which shows a dynamic compression plate.

Intramedullary Nails or Rods: Most intramedullary nailing is done closed with minimal soft-tissue exposure, either in an antegrade or retrograde fashion depending on the fracture site. Both antegrade and retrograde nailing are used for femoral and humeral shaft fractures, and for tibial shaft fractures antegrade nailing is used. The entrance site for an antegrade femoral nail is created in the piriformis fossa; for the retrograde femoral nail, in the intercondylar region; and for the antegrade tibial nail, anteriorly just below the joint line. The nails are introduced over a guide wire, frequently after reaming with flexible reamers to enlarge the intramedullary canal. See FIG. 8, which shows fixation using an intramedullary rod.

Many different designs of intramedullary nails and rods are available. Femoral nails are bowed anteriorly to accommodate the contour of the bone. A majority of nails are cannulated to allow their placement over a guide wire. Intramedullary nails provide excellent stability against bending forces, but they do not control rotation and compressive forces. For the control of rotational forces, proximal and distal interlocking screws are placed (usually in a lateral to medial fashion) through the nail or rod holes in the proximal and distal femur. Interlocking screws increase fixation stability and therefore lead to an increased use of nailing in fracture fixation. Interlocking screws also prevent collapse or shortening of the fracture. If the nail is locked both proximally and distally, it is "statically locked" because all planes of motion are controlled or static. The nail is "dynamically locked" if it is locked at one end only, which allows compression at the fracture site. See FIG. 9, which shows an intramedullary nail with screws.

Flexible intramedullary rods are of smaller diameter and greater flexibility to accommodate different long bone anatomy. Flexible rods are inserted through the metaphysis. They are frequently used for fixation of long bone diaphyseal fractures in skeletally immature patients to avoid placement through the growth plate and subsequent premature closure of the growth plate. Multiple flexible rods, which diverge in the metaphyseal regions, are placed through multiple insertion sites. These rods provide some axial and rotational stability. For small-diameter bones, sometimes a single flexible rod is used. The major disadvantage associated with flexible rods is the frequent need for additional external stabilization such as a plaster cast.

Short intramedullary rods with transversely and obliquely oriented interlocking screws are used for fractures in the diametaphyseal region that extend into the adjacent joint. The weakest points of these intramedullary rods are the distal interlocking screws. In children with osteogenesis imperfecta, two-part telescoping rods are used to allow lengthening of the rod as the child grows.

Potential complications with intramedullary rods include change in bone length, distraction of the fracture site, hardware fracture, hardware loosening, and infection. Intramedullary rods and interlocking screws should not violate the joint surface. The contraindications for intramedullary nailing are local or systemic infection, femoral fractures in patients with multiple injuries, pulmonary trauma (for which temporary stabilization with an external fixation device is recommended) and metaphyseal fractures (for which fixation with interlocking screws may be insufficient to control malalignment). Additionally, because the bone is reamed to insert the rod, there is temporary damage to the internal cortical blood supply which is associated with increased infection rates. There is also an increased rate of pulmonary complications including pulmonary embolism with reaming.

SUMMARY OF THE INVENTION

As noted above, the basic goal of fracture fixation is to stabilize the fractured bone, to enable fast healing of the injured bone, and to return mobility and function of the injured extremity. Fractures can be treated conservatively or with external and internal fixation. Conservative fracture treatment consists of closed reduction to restore the bone alignment. Subsequent stabilization is then achieved with traction or external splinting by slings, splints, or casts. Braces are used to limit range of motion of a joint. External fixators provide fracture fixation based on the principle of splinting. There are three basic types of external fixators: standard uniplanar fixator, ring fixator, and hybrid fixator. There are several types of devices used for internal fixation: wires, pins and screws, plates, and intramedullary nails or rods. Staples and clamps are also used occasionally for osteotomy or fracture fixation.

In accordance with the present invention, there are now disclosed novel intramedullary bone stents which can be used as a means of fracture fixation. Intramedullary bone stents can be made of Shape Memory Alloys (e.g., Nitinol), or other alloys such as Stainless Steel. The intramedullary bone stent is placed into the intramedullary canal, bridging the fracture. As the intramedullary bone stent expands radially, applying hoop stress to the bone, the intramedullary bone stent longitudinally contracts, reducing the fracture and rigidly holding the bone in the correct position. An intramedullary bone stent can be superior to current fixation methods because the intramedullary bone stent can have a modulus of elasticity closer to that of bone, does not create regions of stress shielding, and does not impair blood flow at the fracture site. Additionally, intramedullary bone stents may be beneficial in treating pediatric patients with open growth plates, where nails, rods, and screws may interfere with bone development at the growth plate.

In one preferred form of the invention, there is provided a method for providing stabilization and compression of a bone fracture, the method comprising:

providing an intramedullary prosthesis sized for insertion into the intramedullary canal of a bone and having a distal end, a proximal end and a porous structure therebetween, wherein (i) in a first state, the prosthesis is longitudinally expanded and radially contracted, and (ii) in a second state, the prosthesis is longitudinally contracted and radially expanded, conforms to the shape of the adjacent bone and exerts forces on the adjacent bone; and positioning the intramedullary prosthesis within the intramedullary canal of a bone so that the intramedullary prosthesis spans the bone fracture, whereby to provide stabilization and compression of the bone fracture.

In another preferred form of the invention, there is provided a medical device for reducing fractures, the medical device being configured so that when it is deployed into the intramedullary canal of a bone, the medical device bridges the fracture, expands radially to apply hoop stress to the surrounding bone, and shortens as it expands to pull the fractured ends of the bone together.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 14 is a schematic view showing the CP Stent™ Foreshortening Chart, which indicates that foreshortening is a consequence of the radial expansion of the intravascular stent;

DETAILED DESCRIPTION OF THE PREFERRED EMBODIMENTS

Figure 1:
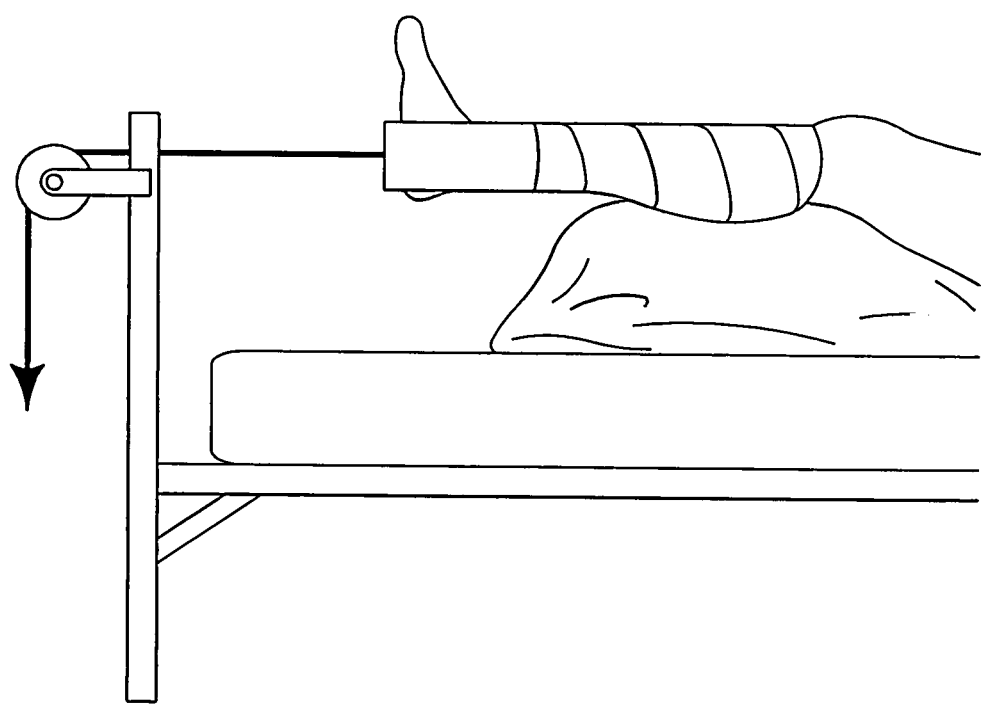
FIG. 1 is a schematic view showing a simple traction device.
Figure 2:
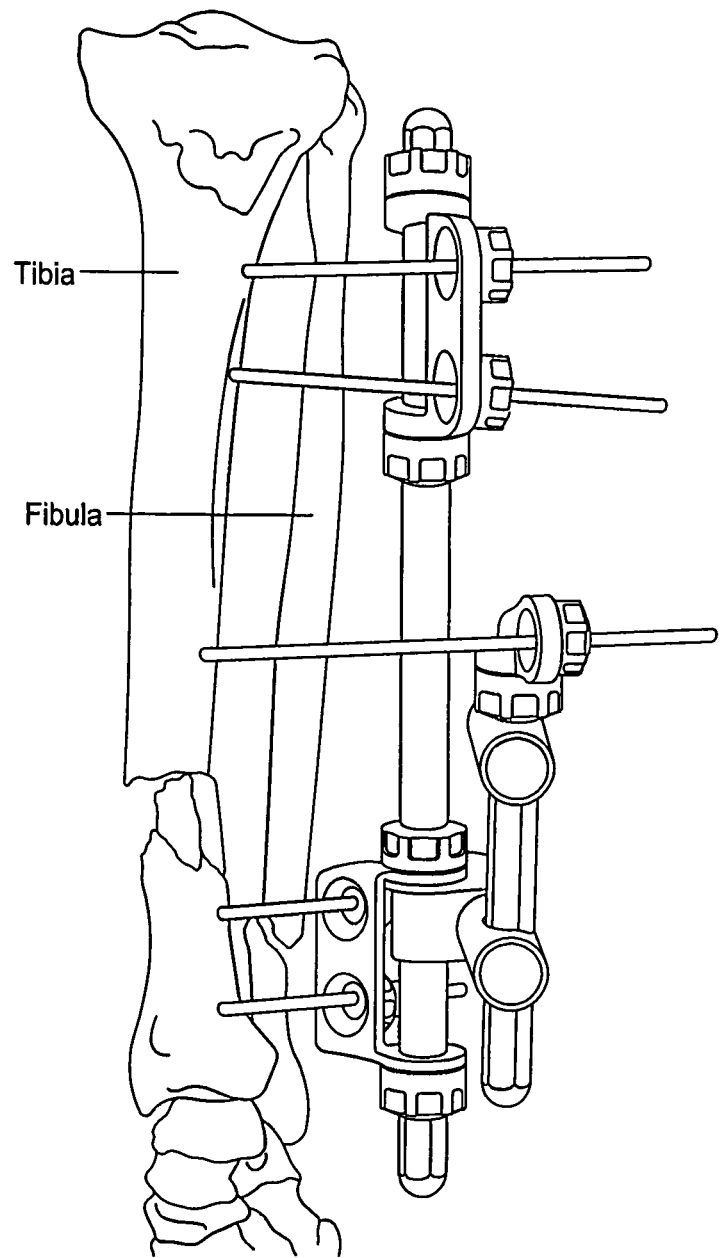
FIG. 2 is a schematic view showing an external fixation device.
Figure 3:
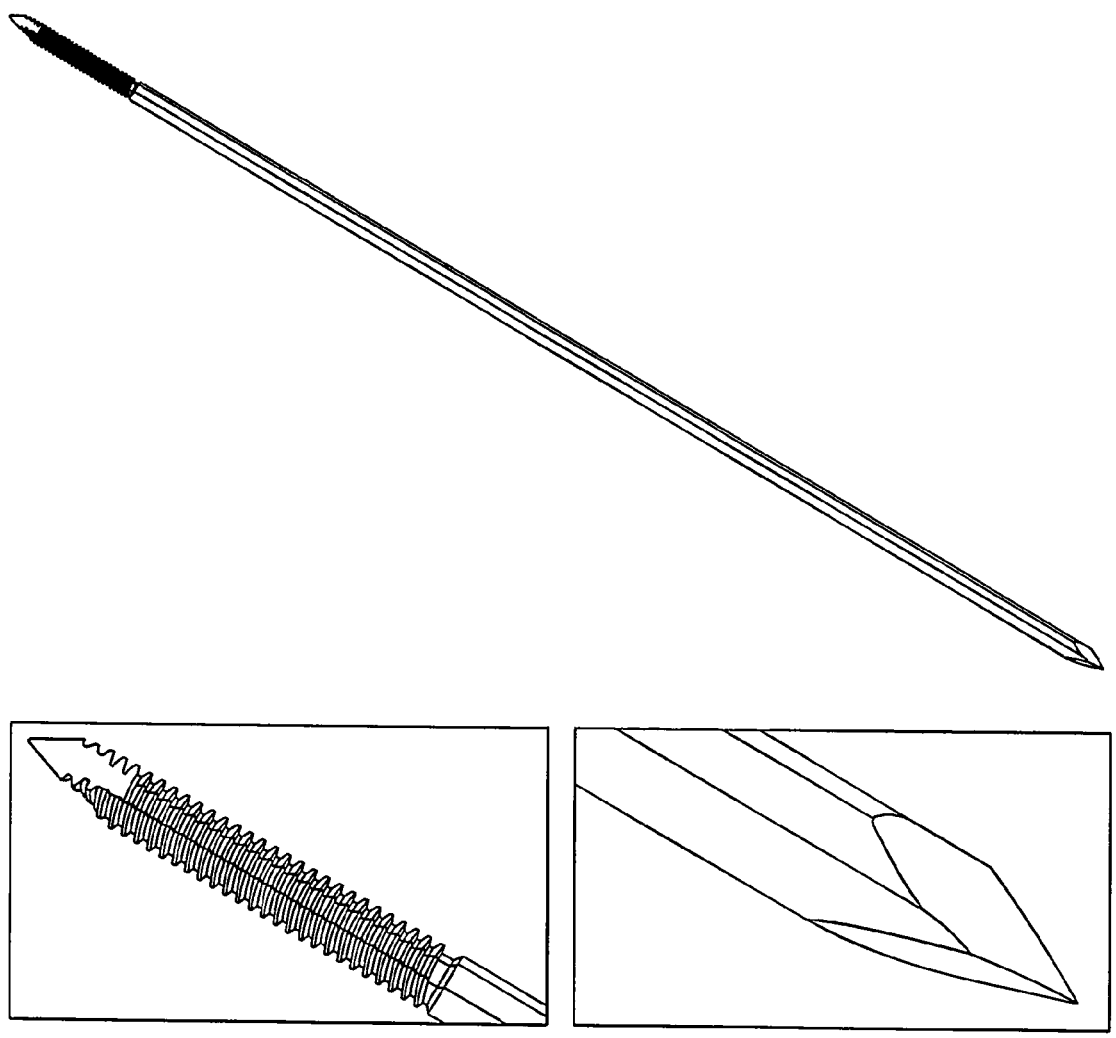
FIG. 3 is a schematic view showing Steinman pins.
Figure 4:
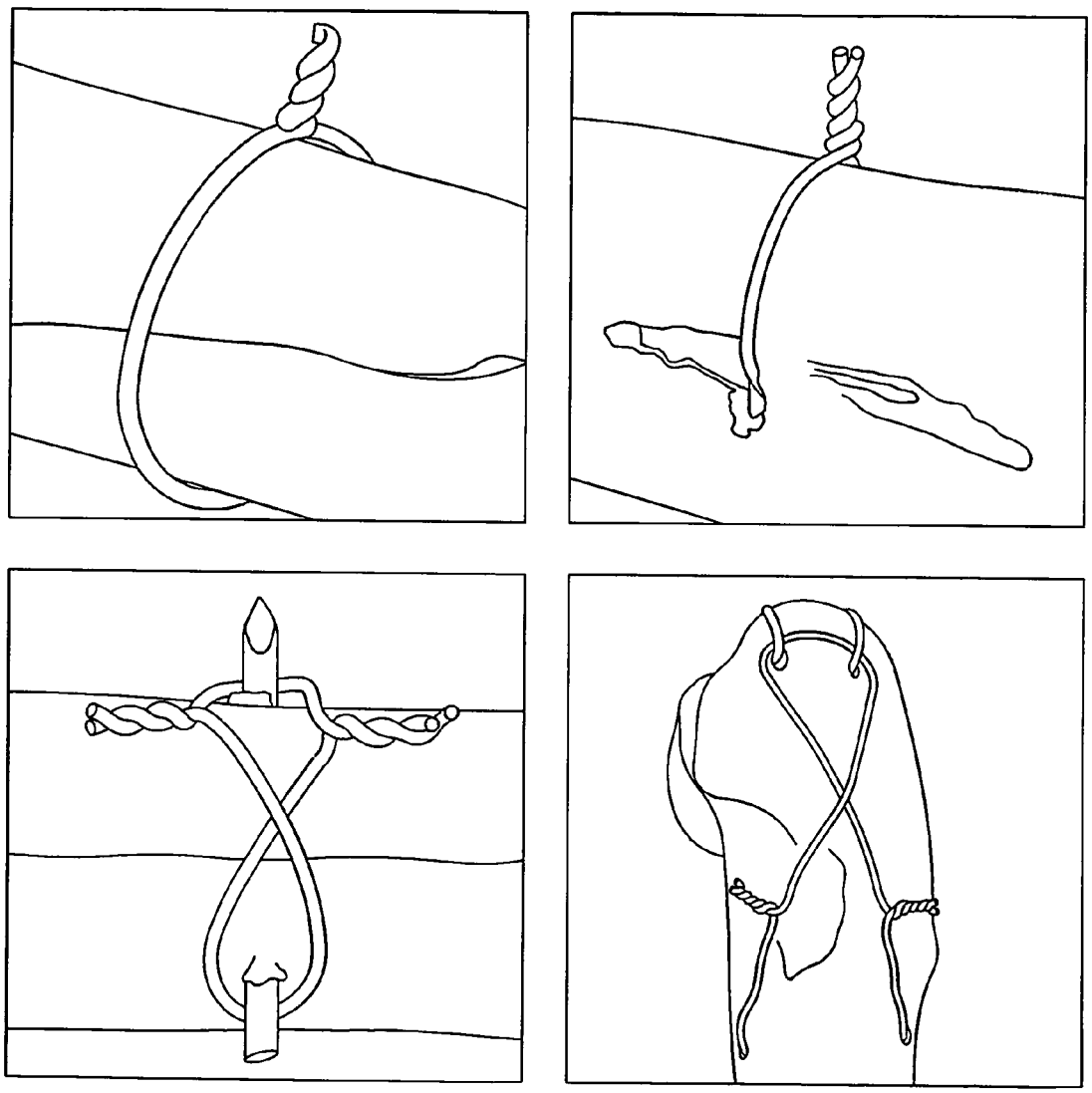
FIG. 4 is a schematic view showing examples of wires used in orthopedic fixation.
Figure 5:
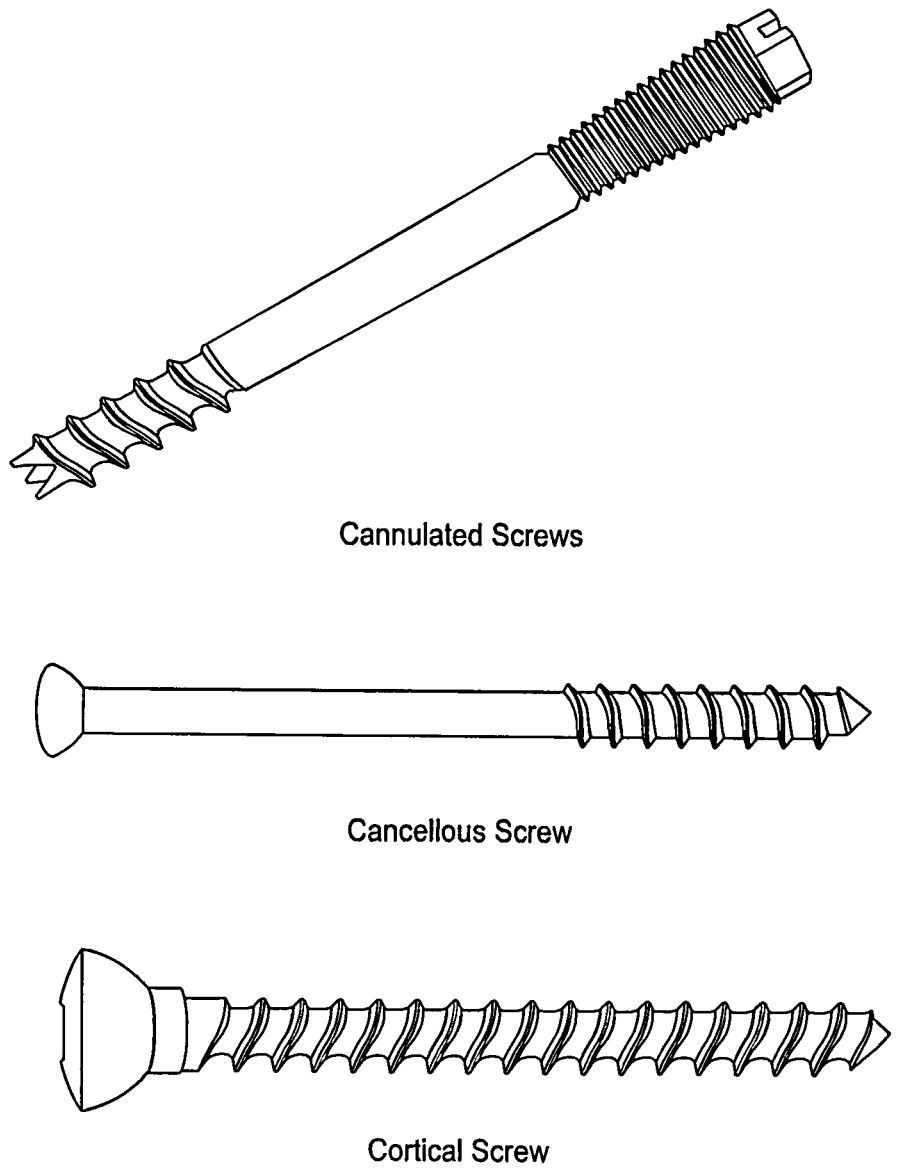
FIG. 5 is a schematic view showing common orthopedic screws.
Figure 6:
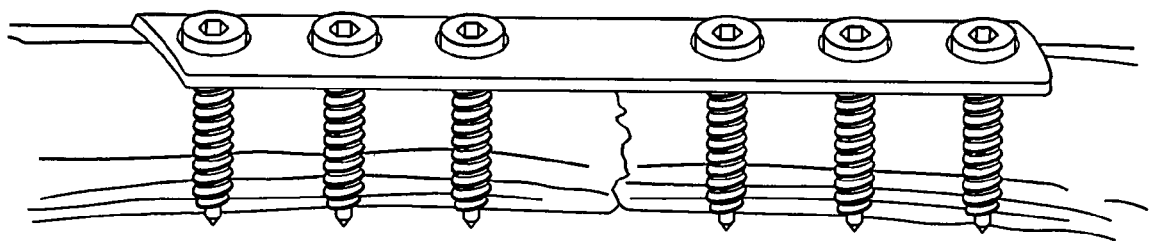
FIG. 6 is a schematic view showing an exemplary orthopedic bone plate.
Figure 7:
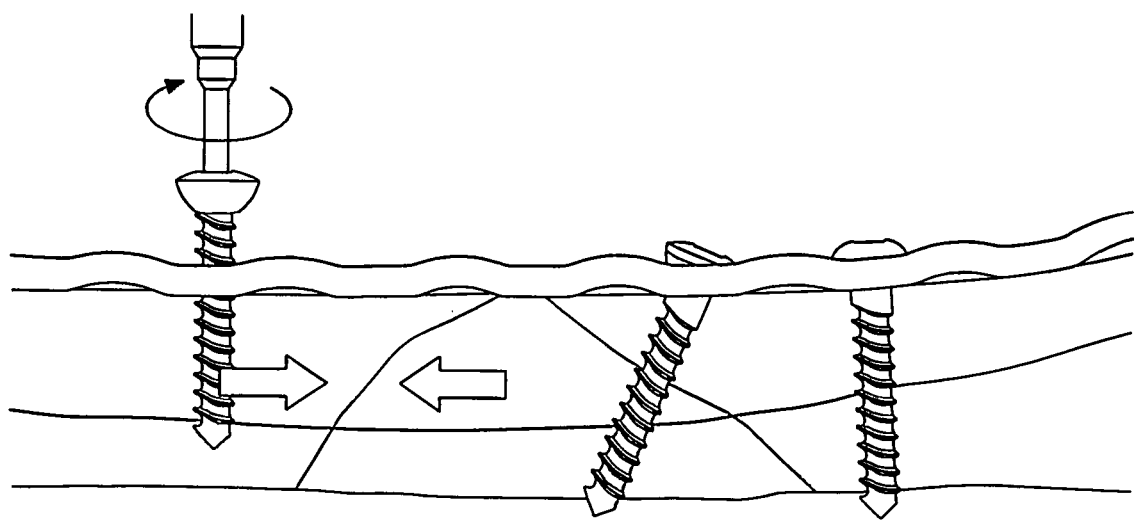
FIG. 7 is a schematic view showing a dynamic compression plate.
Figure 8:
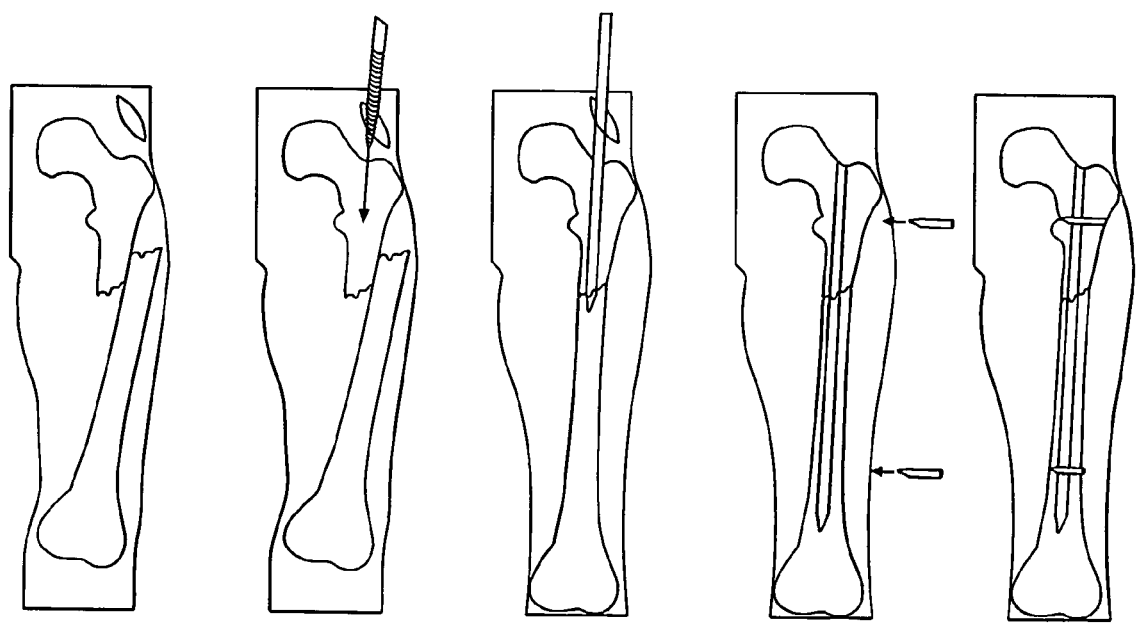
FIG. 8 is a schematic view showing fixation using an intramedullary rod.
Figure 9:
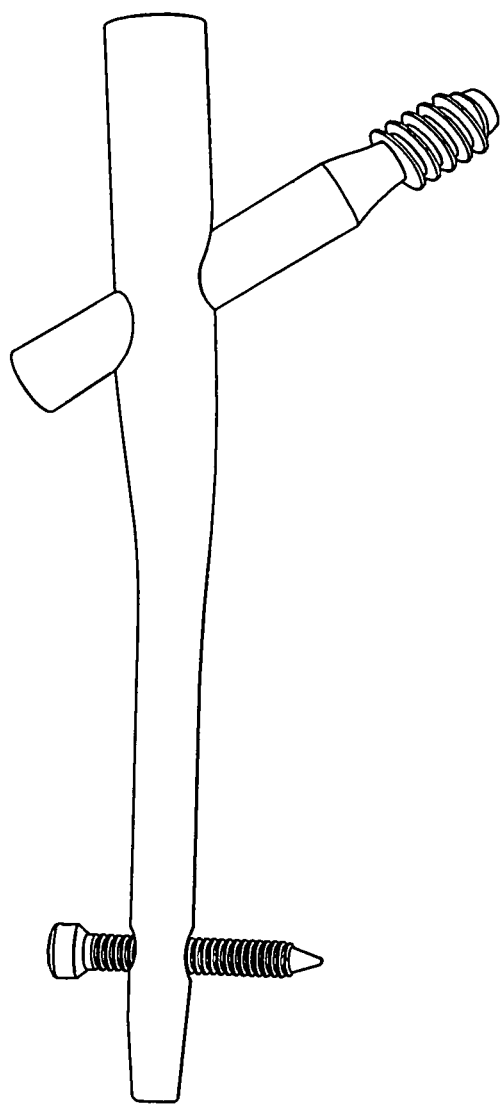
FIG. 9 is a schematic view showing an intramedullary nail with screws.
Figure 10:
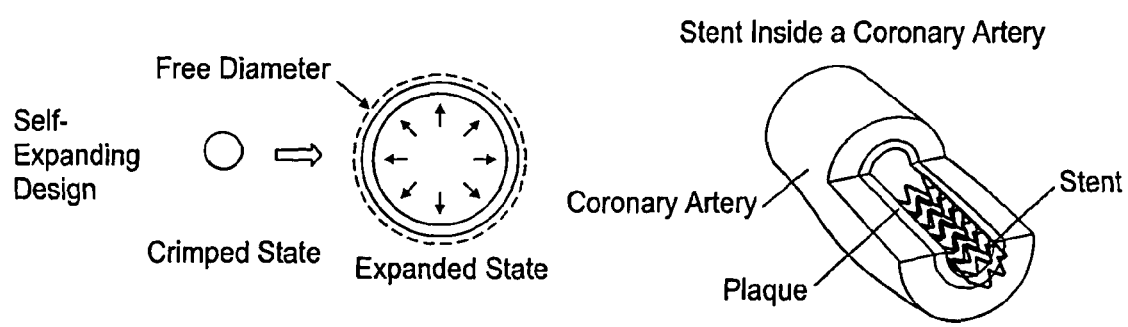
FIG. 10 is a schematic view showing expanding stents used in blood vessels.

Novel Intramedullary Bone Stents: Intravascular stents are commonly used in arteries to hold the artery open, e.g., to treat stenosis caused by a buildup of plaque on the walls of the artery. Thus, these intravascular stents are designed to maintain patency of the blood vessel. Intravascular stents are inserted into the artery in a crimped state and expanded to a larger diameter. See, for example, FIG. 10, which shows expanding stents used in blood vessels. To date, stents have not been used in orthopedic applications to reduce a fracture site.

Figure 11:
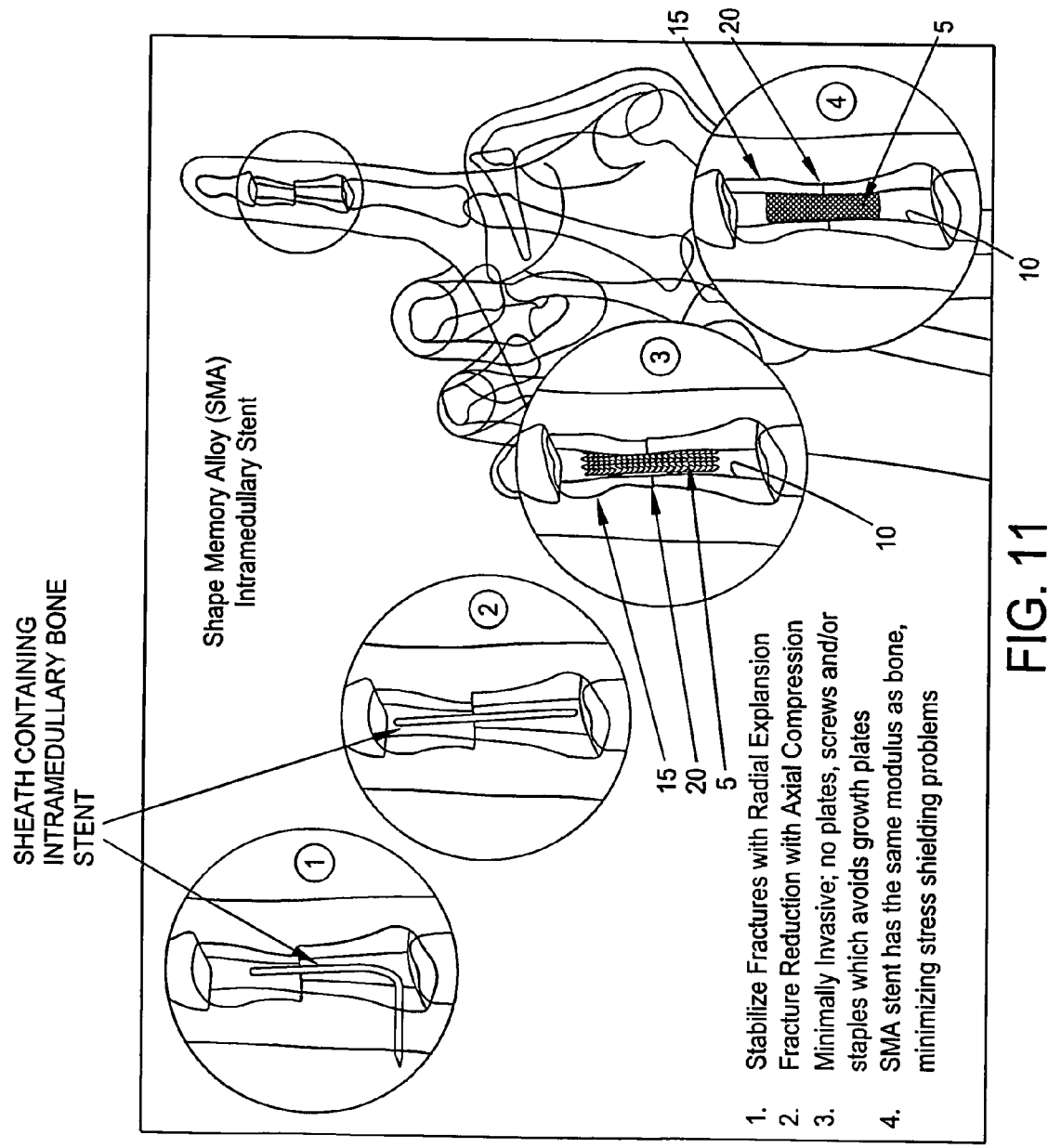
FIG. 11 is a schematic view showing an intramedullary bone stent stabilizing and reducing a fracture.

In accordance with the present invention, and looking now at FIG. 11, there is shown an intramedullary bone stent 5. Intramedullary bone stent 5 is placed into the intramedullary canal 10 of a bone 15, bridging the fracture 20. As the intramedullary bone stent 5 expands, applying hoop stress to the bone 15, the intramedullary bone stent 5 shortens, reducing the fracture 20 and rigidly holding the bone 15 in the correct position. In one preferred form of the invention, the intramedullary bone stent 5 is formed out of a shape memory alloy (SMA). An intramedullary bone stent 5 can be superior to current fixation methods because the intramedullary bone stent 5 can have a modulus of elasticity closer to that of bone, does not create regions of stress shielding, and does not impair blood flow at the fracture site. Additionally, intramedullary bone stents 5 may be beneficial in treating pediatric patients with open growth plates, where nails, rods, and screws may interfere with bone development at the growth plate.

Figure 12:
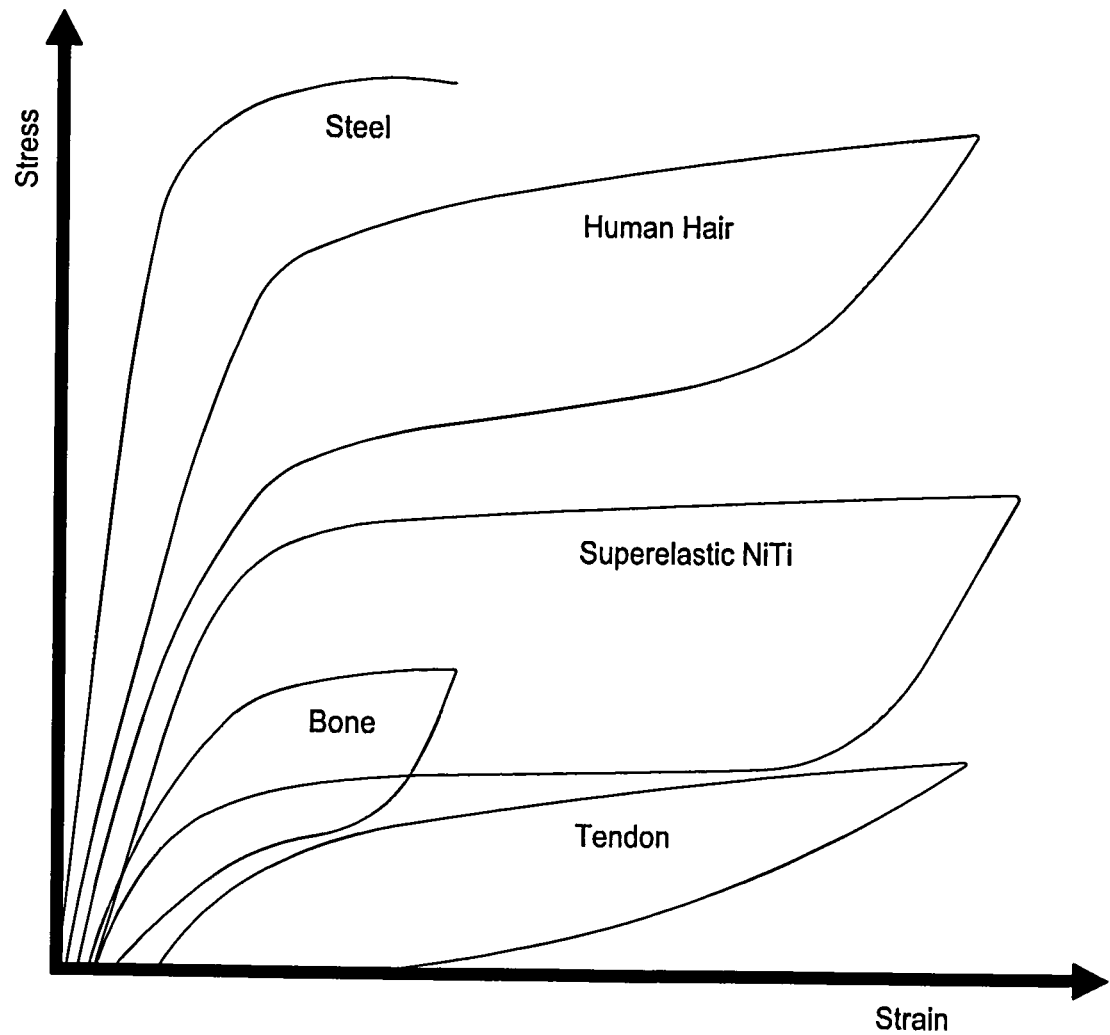
FIG. 12 is a schematic view showing the stress-strain properties of Nitinol, with comparison being made to various materials.

Shape Memory Material (e.g., Nitinol) Stent: From its earliest use in orthodontic arch wires to its more-recent dominant role in cardiovascular implants such as intravascular stents, endografts, and filters, shape memory materials (e.g., Nitinol, Titanium-Niobium, and shape memory polymers) all possess unique properties that have made it the material of choice for a variety of medical applications. The vast majority of medical applications take advantage of Nitinol's (NiTi's) unusual superelastic properties. More particularly, while conventional engineering materials typically have an elastic limit much less than 1% strain, Nitinol can experience fully recoverable strains up to 8%. See FIG. 12, which shows the stress-strain properties of Nitinol, with comparison being made to various materials.

This superelastic capability allows a properly designed Nitinol component to radically transform its shape during service, fueling the trend toward minimally invasive procedures. For example, a Nitinol intravascular stent may be designed to be delivered through a 2-mm sheath and expand to support a 10-mm vessel. Similarly, an endoscopic instrument may be delivered through a 15-mm opening, expand to 60 mm to retrieve a specimen, and then collapse to exit through a similarly sized port. In short, if a medical component must be delivered in a compressed state and then become an expanded shape, Nitinol is likely to offer design advantages unavailable with other materials.

Today there are a wide range of intravascular prostheses on the market for use in the treatment of aneurysms, stenosis, and other vascular irregularities. Balloon expandable (i.e., non-Nitinol) and self-expanding intravascular stents (i.e., Nitinol) are well known for restoring patency in a stenosed vessel, e.g., after an angioplasty procedure, and the myriad usages of coils and stents are known techniques for treating aneurysms. The biocompatibility of Nitinol has been well documented. In Nitinol, Nickel and Titanium are distributed in a regular crystal lattice order, exhibiting high atomic bonding forces with mixed covalent and metallic character, thus it is difficult for nickel to leave the bulk material. The surface of NiTi is well passivated because Titanium is more readily oxidized than Nickel. NiTi devices exhibit a Ti-based oxide layer which is responsible for the corrosion resistance of this material and acts as an effective barrier to nickel ion release. From a biological point of view, the integrity of the outermost surface layer and its ability to repassivate are crucial importance for the biocompatibility of NiTi.

Figure 13:
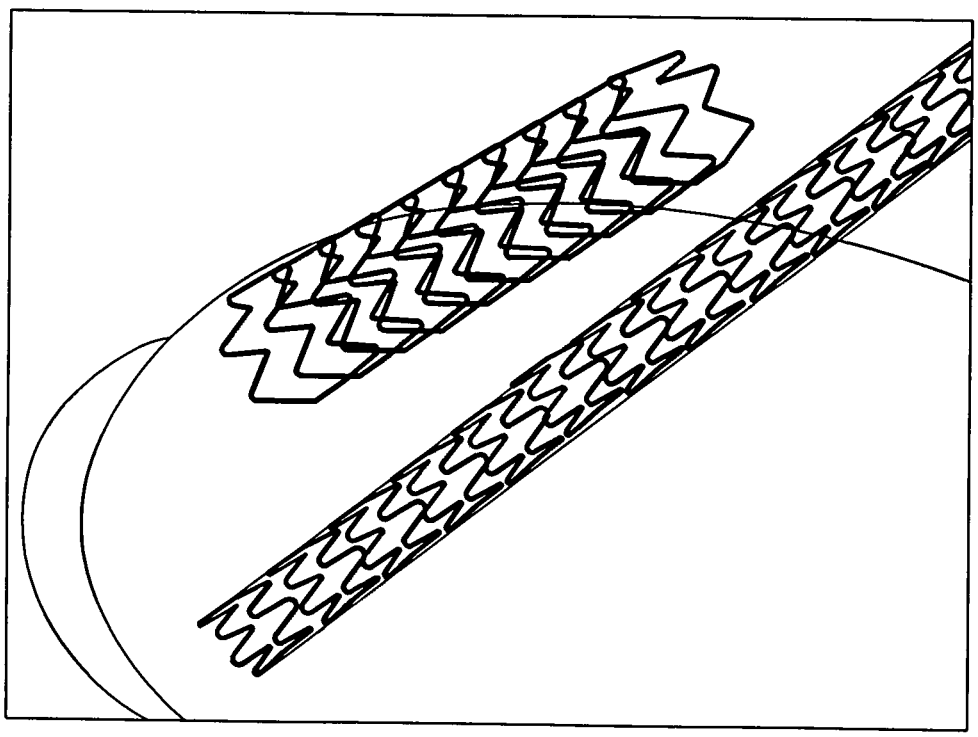
FIG. 13 is a schematic view showing the radial expansion of a Nitinol intravascular stent.

Self-expanding intravascular stents generally are retained in a contracted delivery configuration using a sheath, then the Nitinol intravascular stent self-expands when the sheath is retracted. Such NiTi stents commonly have a major drawback in intravascular applications, for example, the intravascular stents may experience large length shrinkage during radial expansion (referred to as "foreshortening") and may shift within the blood vessel prior to engaging the blood vessel wall, resulting in improper placement. The reason that intravascular stents become shorter during radial expansion is because the angles of the struts within the intravascular stents increase (from parallel to the centerline of the stent to an angle of 15°-60° to the centerline of the stent) when the intravascular stents expand radially, thereby shortening the length of the intravascular stents. In other words, the intravascular stent is made of a series of "Zs", and when the intravascular stent is collapsed, the "Z's" are flat and look more like dashes. During radial expansion of the intravascular stent, the dashes open to Z's, shortening the intravascular stent. See FIG. 13, which shows the radial expansion of a Nitinol intravascular stent.

Foreshortening is explained in terms of a deformation in longitudinal direction after expansion of the stent. It is calculated as follows:

$$\text{Foreshortening} = \frac{L - L_{unloaded}}{L}$$

$L$ = Original Length of Stent $L_{unloaded}$ = Length after removing catheter

As seen in the CP Stent™ Foreshortening Chart shown in FIG. 14, foreshortening is a consequence of the radial expansion of the intravascular stent.

The success of vascular stents in the restoration of blood flow is limited by restenosis. Recent data generated from computational fluid dynamics (CFD) models suggest that the vascular geometry created by an implanted stent causes local alterations in wall shear stress (WSS) that are associated with neointimal hyperplasia (NH). Foreshortening is a potential limitation of intravascular stent design that may affect intravascular stent performance and the rate of restenosis. The angle created between axially aligned stent struts and the principal direction of blood flow varies with the degree to which the intravascular stent foreshortens after implantation. Progressive degrees of intravascular stent foreshortening are also associated with strut misalignment relative to the direction of blood flow as indicated by analysis of near-wall velocity vectors, suggesting that foreshortening may predispose the stented vessel to a higher risk of neointimal hyperplasia. Additionally, during foreshortening, there can be unfavorable shearing between the stent struts and the vascular wall, potentially causing hemorrhaging.

There are dozens of metal and bioresorbable intravascular stent designs on the market today (see http://www.nitinol.com/media/reference-library/009.pdf), and intravascular stent designers have been working to overcome the aforementioned foreshortening problem of intravascular stents for many years. See, for example, U.S. Pat. No. 6,761,731 "Balloon-stent interaction to help reduce foreshortening".

Intramedullary Bone Stent: The present application relates generally to the provision and use of novel intramedullary bone stents to repair a bone fracture and facilitate bone fusion by the intramedullary stent's radial expansion and axial compression during foreshortening. In one preferred form of the invention, the novel intramedullary bone stents are formed out of shape memory material (e.g., Nitinol). Thus, in one preferred form of the invention, there is provided an osteosynthetic Nitinol intramedullary bone stent implant for disposition within the intramedullary canal of a bone, whereby to span a fracture line, and effect fracture/fusion repair. The novel fracture repair devices, systems, and methods of the present invention also include those for repairing intentional fracture sites, such as but not limited to osteotomies created for reconstructive purposes. Bony fusions of surgically resected joints throughout the body are also within the scope of the present invention. Such Nitinol intramedullary bone stent fracture fixation devices, systems and methods of the present invention help maintain compressive loads across the fracture site for longer periods of time compared to prior devices.

Figure 15:
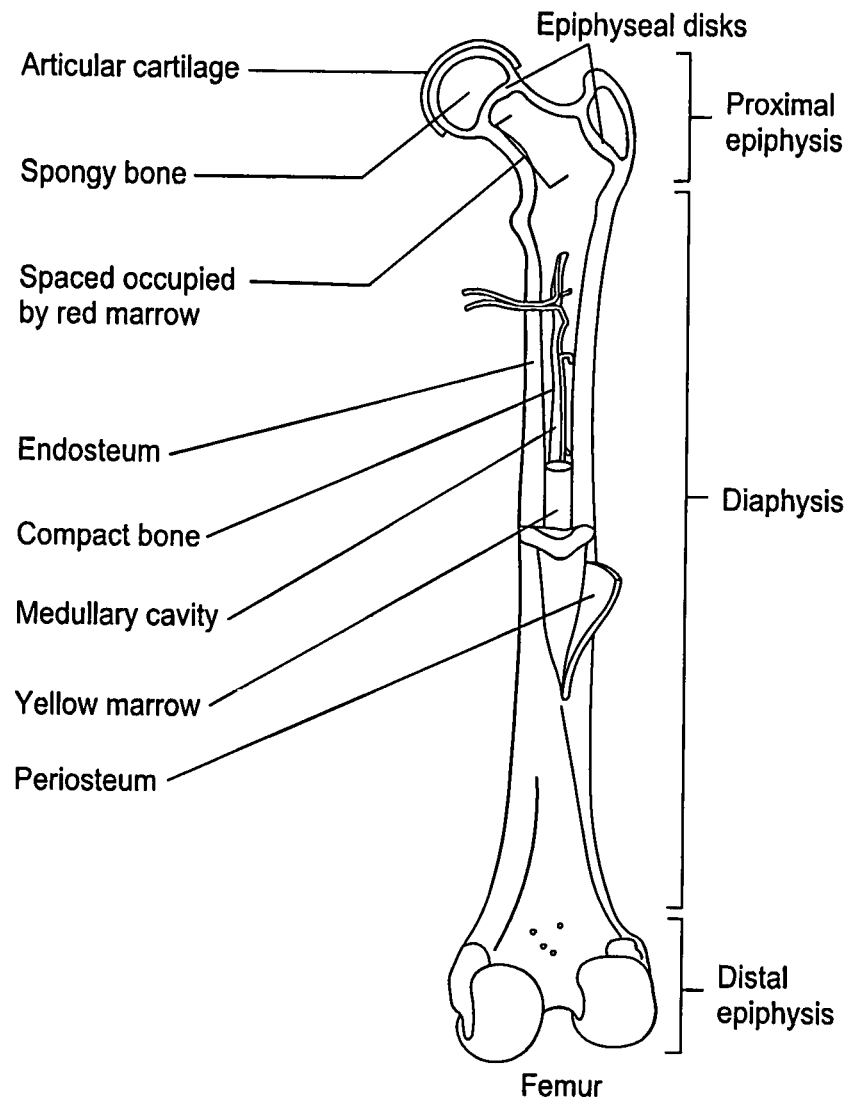
FIG. 15 is a schematic view showing the anatomy of the medullary cavity of the femur.

The novel bone stent is an intramedullary device. More particularly, the medullary cavity (medulla, innermost part) is the central cavity of a bone shaft where red bone marrow and/or yellow bone marrow (adipose tissue) is stored; hence, the medullary cavity is also known as the marrow cavity. Located in the main shaft (cortical bone) of a long bone (diaphysis), the medullary cavity has walls composed of spongy bone (cancellous bone) and is lined with a thin, vascular membrane (endosteum). However, the medullary cavity is the area inside any bone (long, flat, etc.) that holds the bone marrow. The clavicle is the only long bone that does not contain a medullary cavity. This area is involved in the formation of red blood cells and white blood cells. See FIG. 15, which shows the anatomy of the medullary cavity of the femur.

The intramedullary bone stent, preferably made of shape memory materials such as Nitinol, can be used to support, stabilize and reduce bone fractures (see FIG. 11). The benefits of an intramedullary bone stent appliance include:

The intramedullary bone stent uniformly conforms to the intramedullary geometry and uniformly expands and locks, both axially and radially, along the length of the bone, which minimizes or eliminates interfragmentary motion. There is a widely held opinion that interfragmentary sliding (shear) motion is detrimental to the repair of bone fractures.

In order for a fracture to heal, it needs stability and blood flow. Blood brings the components for healing to the fracture site. These include oxygen, healing cells, and the body's own substances necessary for healing (e.g., growth factors). The blood supply to the injured bone usually comes back on its own during the healing period. The use of an intramedullary bone stent, without screw holes, compressive plates, or invasive nails, allows for a near normal blood supply to the fracture site by reducing or minimizing additional vascular damage.

The sustained compressive therapy offered by the intramedullary bone stent can also be osteoinductive, due to its piezoelectric effects on osteoblasts themselves. The intramedullary bone stent is designed to apply compressive forces at the fracture site, by foreshortening and/or training the NiTi to pull the bone segments in compression. The intramedullary bone stent, however, is "spring-like", and will oscillate and vibrate to some extent, causing mechanical loading to catalyze osteoblast, bone remodeling and fracture healing.

In pediatrics, where it is often difficult to use an intramedullary device because of the concern of disrupting the growth plate, a fracture through the growth plate requires perfect reduction, and pinning may be necessary. Rotational malalignment in the fingers is a frequent complication and can be easily detected after reduction by flexing all the fingers together. Fingers should be immobilized by syndactylization, or "neighbor strapping", with the adjacent finger for a maximum of three weeks. A short forearm cast with an aluminum splint is another alternative. Physical therapy might be necessary. In the younger child, more durable immobilization should be used to prevent the child from removing it. Open reduction for phalangeal fractures is required for displaced intra-articular fractures and oblique, shortened midshaft fractures. NiTi intramedullary bone stents can traverse the growth plate with a collapsed intramedullary bone stent diameter comparable to the size of a large needle, minimizing damage to the growth plates. Now, using an intramedullary bone stent, the intramedullary fixation becomes feasible in children for the first time.

When a conventional bone fracture compression plate made of high modulus 316L stainless steel (200 GPa) relative to cortical bone (15 GPa) is used, this results in stress-shielding the bone under the plate and is believed to cause osteoporosis that weakens the bone under the plate. Relieving the bone from carrying a load over an extended period of time is believed to contribute to the development of this type of osteoporosis, also known as osteopenia. When the plate and screws are removed from the healed bone, the bone may re-fracture due to the weakening which resulted from the development of osteoporosis or osteopenia.

Figure 16:
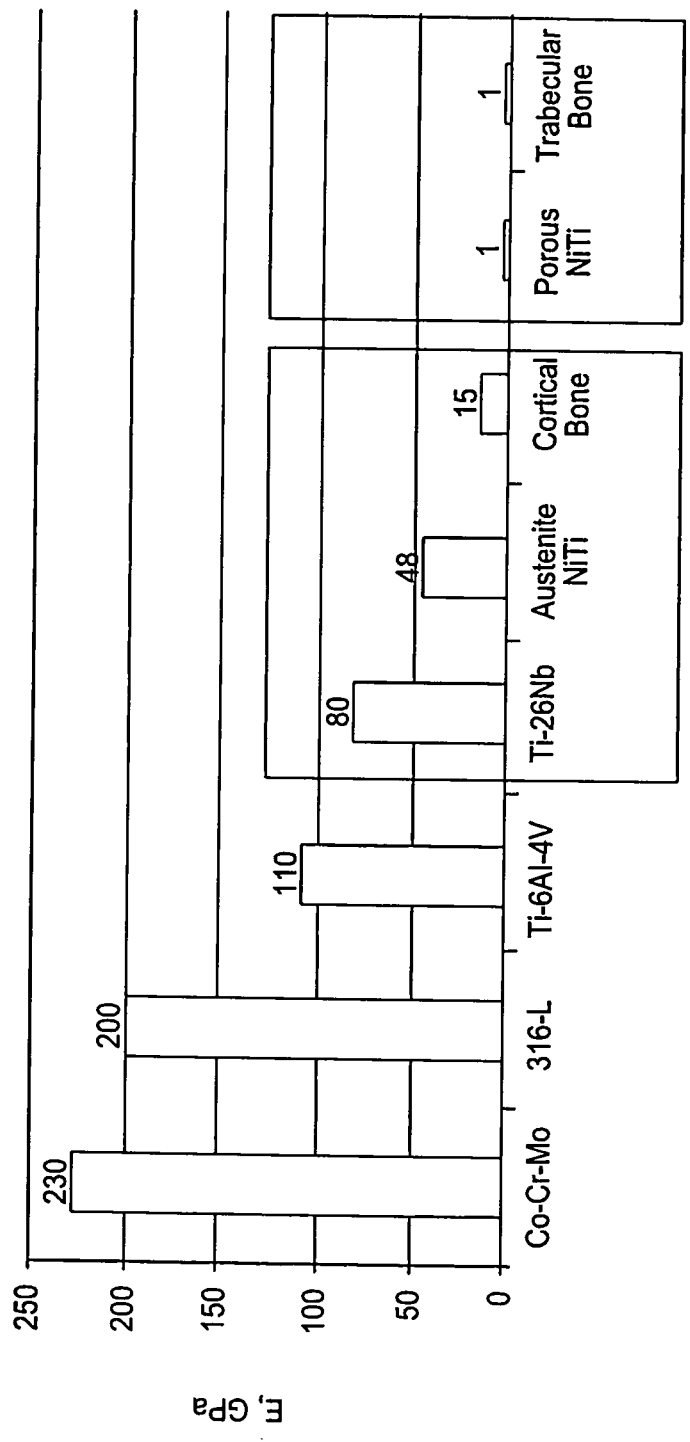
FIG. 16 is a schematic view showing the measure of the stiffness or modulus of elasticity of various materials.

Unlike 316-L stainless steel and Titanium (Ti 6Al-4V), Nitinol has a very similar elastic modulus compared to bone, in the range of 5 GPa to about 70 GPa. The NiTi intramedullary bone stent material will more naturally load the fracture site because it has a stiffness close to human tissue so that stress shielding does not occur which is a problem with stiff plates and IM nails. See FIG. 16, which is a chart showing the measure of the stiffness or modulus of elasticity of various materials.

Figure 17:
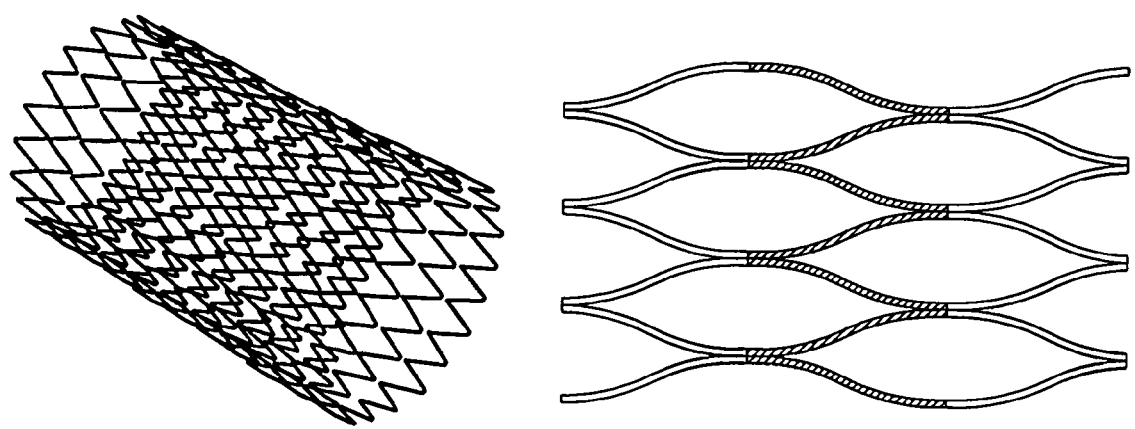
FIG. 17 is a schematic view showing struts shaped like a "Z" that can be used to make up the structure of an intramedullary bone stent of the present invention.

In addition to NiTi having a similar modulus of elasticity to bone, the intramedullary bone stent's stiffness can be designed to have comparable stiffness to bone by changing the dimensions of the intramedullary bone stent, i.e., strut thickness, strut width, strut angle and strut frequency. FIG. 17 shows struts shaped like a "Z" that can be used to make up the structure of an intramedullary bone stent of the present invention.

Figure 18:
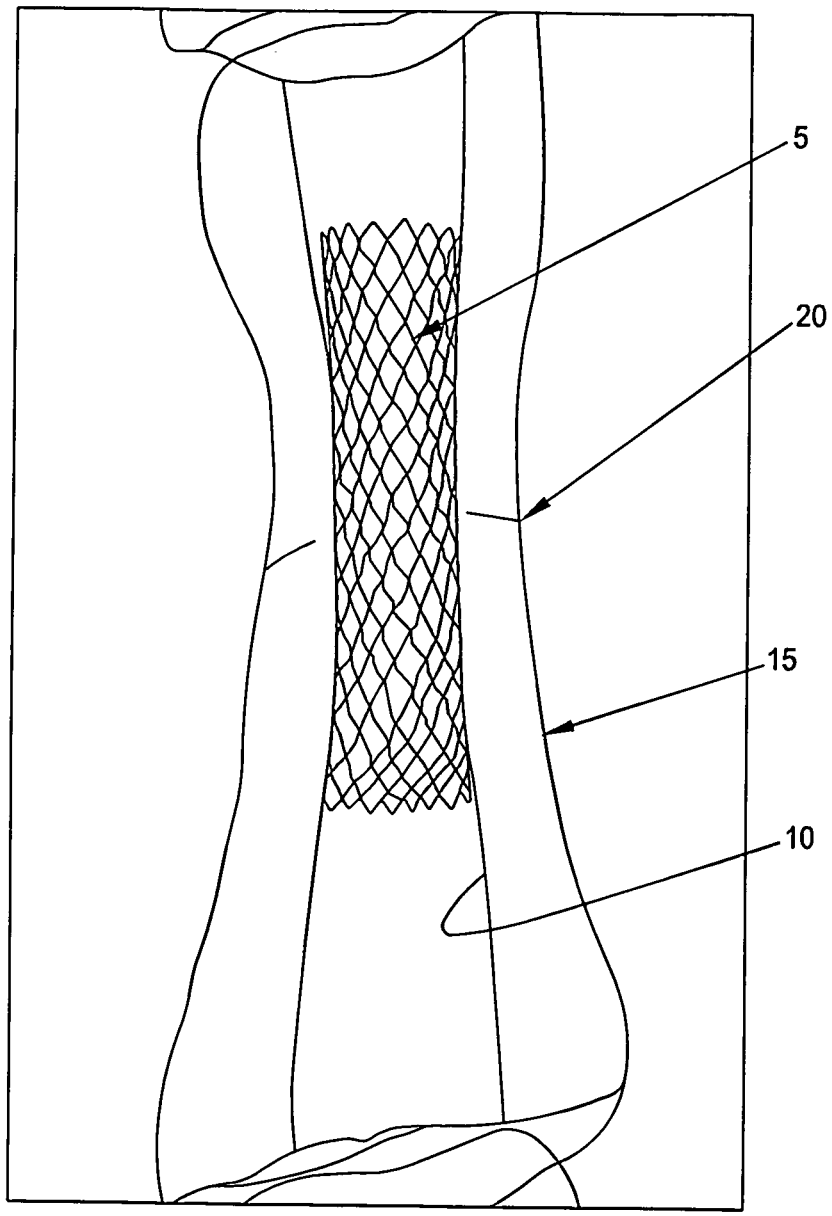
FIG. 18 is a schematic view showing an intramedullary bone stent stabilizing and reducing a fracture.

Thus, in accordance with the present invention, and looking now at FIG. 18, an intramedullary bone stent 5 is restrained in a radially-contracted, longitudinally expanded condition (e.g., within a sheath, not shown), advanced down the intramedullary canal 10 of a bone 15 so as to span a fracture line 20, and then the restraint of the intramedullary bone stent 5 is released, so that the intramedullary bone stent radially expands to grip the surrounding bone and longitudinally contracts so as to place the bone fragments in compression, whereby to facilitate healing of the fracture. Preferably, intramedullary bone stent 5 is formed out of a shape memory material so that the intramedullary bone stent 5 has a modulus of elasticity similar to that of bone, whereby to minimize stress shielding and thereby enhance bone healing.

Figure 19:
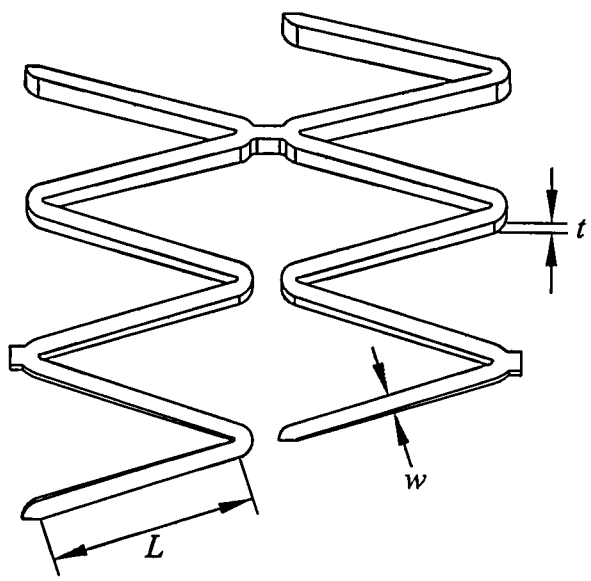
FIGS. 19 and 20 are schematic views showing the strain and force characteristics for a simple beam of the type used in an intramedullary bone stent.
Figure 20:
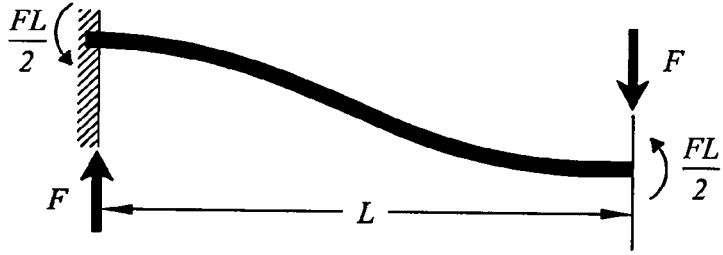

Unlike a conventional intramedullary nail, the force of the expanding Ni—Ti intramedullary bone stent can be engineered to apply enough radial force to stabilize the fracture yet be somewhat flexible in areas away from the fracture site. See FIGS. 19 and 20, which show the strain and force characteristics for a simple beam of the type used in an intramedullary bone stent.

Figure 21:
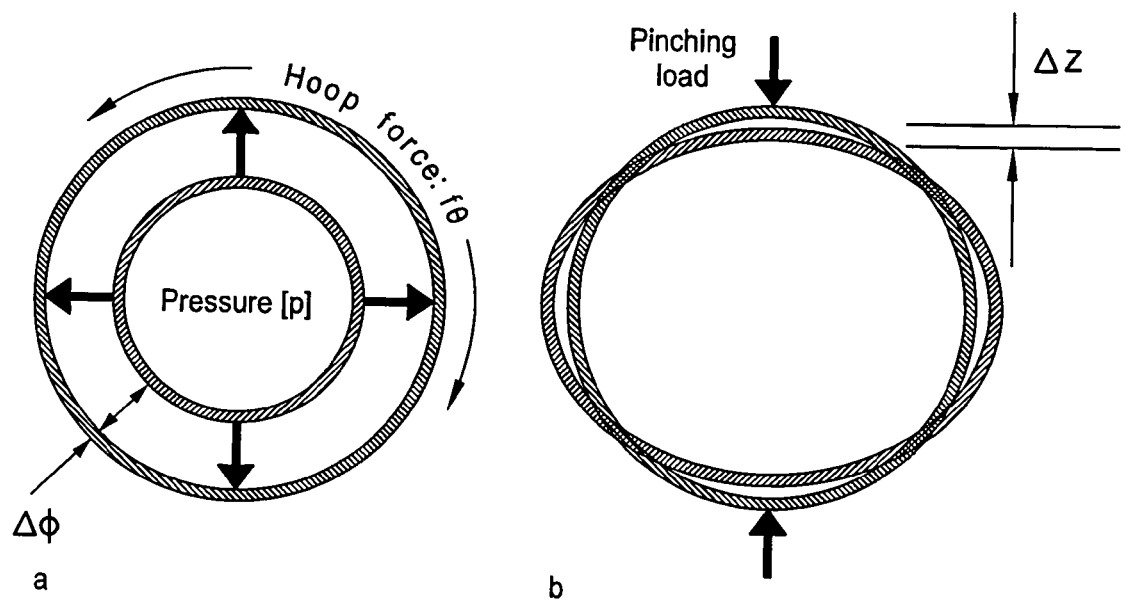
FIG. 21 is a schematic view showing the calculations for the hoop and bending stiffness of an intramedullary bone stent.

In addition, the expanding radial hoop force can be engineered to overcome the collapse, buckling and/or pinching loads at and near the fracture site. See FIG. 21, which shows the calculations for the hoop and bending stiffness of an intramedullary bone stent.

Figure 22:
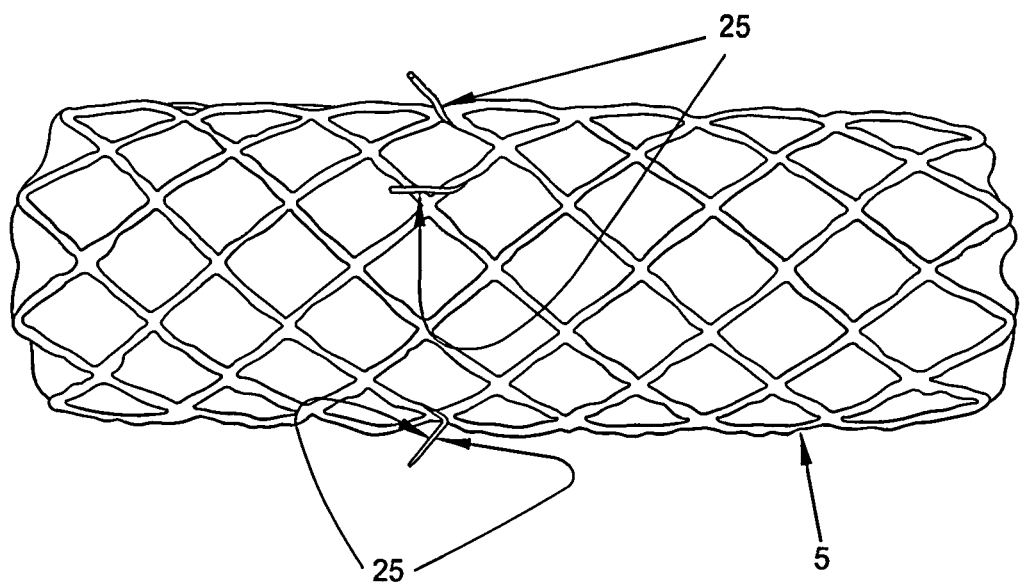
FIG. 22 is a schematic view showing a Nitinol intramedullary bone stent having integral barbs for gripping the inner wall of the host bone.

Stent Foreshortening To Create Dynamic Interference Fit With Compressive Loads Against The Fracture Site: When an intravascular stent is deployed in an artery or vein, it radially expands and simultaneously shortens, which can cause the intravascular stent to undesirably tear the wall of the artery or vein as the intravascular stent foreshortens. Thus, in vascular applications, foreshortening is problematic and undesirable—and much effort has gone into minimizing the negative effects of foreshortening. In the case of the present invention, where an intramedullary bone stent is provided, the struts of the intramedullary bone stent can intentionally be made with barbs or tangs so as to aggressively grip the surrounding bone tissue in order to pull the bone fragments on either side of the fracture together, effectively compressing the bone fracture when stent foreshortening takes place. See, for example, FIG. 22, which shows a Nitinol intramedullary bone stent 5 having integral barbs 25 for gripping the inner wall of the host bone. Thus, the present invention advantageously harnesses the foreshortening effect to provide desired compression. The tension applied by the shortening intramedullary bone stent to the bone may better maintain close apposition of the bone fragments, and better establish compression across the fusion zone, during the healing process. In this respect it will be appreciated that bones in contact with each other, and under compressive load, heal together faster than bones held apart.

Significantly, with the present invention, the novel shape memory alloy intramedullary bone stent is longitudinally stretched (and radially contracted) during the insertion procedure, e.g., by loading the intramedullary bone stent within a constraining sheath. Once the intramedullary bone stent is properly positioned within the intramedullary canal (which is done manually, while being viewed via fluoroscopy), the shape memory alloy intramedullary bone stent is released from its constraint so as to radially expand and longitudinally contract, whereby to engage the bone fragments on opposing sides of the fracture line and draw them together in compression. This action maintains the target fusion bones in close apposition. The NiTi intramedullary bone stent offers sustained compression for longer time periods than static, non-adaptive intramedullary devices. Unlike plates and screws, the NiTi intramedullary bone stent will maintain compressive load across the fracture site well after the fracture is healed. The intramedullary bone stent will not compromise blood flow because holes in the bone are not created from screws and or staples, nor will they apply deleteriously localized stresses concentrations in small areas like bone staples and screws do. Furthermore, because the intramedullary bone stent is contained wholly within the bone, the NiTi intramedullary bone stent will not cause tissue scaring like bone screws and staples do.

The NiTi intramedullary bone stent of the present invention can create ample compressive forces on the bone tissue that can stimulate rapid bone regeneration in order to fill in deficient bone fractures or to fix an implant firmly within adjacent bone. To succeed, the NiTi intramedullary bone stent must be habitable, especially for bone-forming cells (e.g., osteoblasts) such that they can colonize on the strut surfaces and synthesize new bone tissue. Additionally, osseointegration is preferred in the spaces between the struts. For successful implants, sufficiently regenerated bone fills the gap between an implant and juxtaposed bone, thus the implant is attached firmly with the surrounding bone. Frequently implant materials are not compatible with bone cell responsible for bone formation, but rather they promote the formation of undesirable soft connective tissue. Fibrous soft tissue, as opposed to hard bony tissue, has been shown to improperly fix orthopedic implants into surrounding bone which leads to loosening under physiological loading conditions and eventual implant failure.

The NiTi intramedullary bone stent offers surgeons the ability to eliminate traditional device performance issues that can negatively impact the ability to achieve a solid fusion.

Osteoblast Response To Mechanical Strain: The mechanical environment of a fracture site has been known to play an important role in fracture healing and tissue differentiation for many years. Appropriately applied mechanical conditions have been known to accelerate fracture healing and there are many mechanical properties that influence the healing process including strain rate, frequency, magnitude, number of cycles, and number of days of stimulation among others. The majority of investigations into the effects of the local mechanical environment on bone repair actively control the motion at the defect. These devices allow for a prescribed motion at set time points. Normally, these devices are powered by an external actuator or through a sliding mechanism that allows a set motion to occur during normal ambulation, which is called dynamization. Studies using this model have found that larger fracture gap sizes lead to poorer fracture healing and that gap size plays a significant role in the progression of repair. These studies also showed that small controlled movements in smaller gaps can increase bone formation, callus size and tensile strength. The disadvantages of this model are that the motion is limited to compressive strains and, over time, the motion will decrease as healing progresses and tissues progressively fill the defect, altering the experimental conditions.

This same conclusion was drawn in studies applying a variety of different controlled micromotions at many different frequencies, as well as with applied axial dynamization. Studies suggest that changing the mechanical environment in a healing fracture provides strong evidence that micromotion plays a vital role in fracture repair; however, too large of interfragmentary motion disrupts fracture repair. Some researchers believe that bone formation occurs in areas of low to moderate tensile strain, cartilage formation occurs under hydrostatic pressure, and fibrous tissue growth occurs in areas of moderate to high tensile strain. And some researchers have hypothesized that small strains and small hydrostatic pressures ($<\pm 0.15$ MPa) lead to direct bone formation, compressive hydrostatic pressures above 0.15 MPa lead to chondrogenesis and therefore endochondral ossification, and all other stimuli lead to connective tissue or fibrocartilage formation. NiTi intramedullary bone stents can be designed to create both compressive and tensile force at the fracture site, being stiff to stabilize but just flexible enough to cause ample hydrostatic pressure ($<\pm 0.15$ MPa) to create direct bone formation at the fracture site.

Types Of Stents: There are a number of different types of devices for stenting of body passages. These may be classified into two general categories: expandable meshes, which include self-expanding types and non-self-expanding types, and non-expandable meshes, which are typically made of plastic or polymeric material. The self-expanding meshes can be made of a material, such as Nitinol, which changes configuration upon heating to body temperature, and exhibits superelastic behavior. Other self-expanding meshes are made of resilient mesh material which can be flexed down into a small diameter tube and held in place in such a configuration until it is released, at which time it expands to a larger diameter configuration. The non-self-expanding meshes are expanded by use of an inflatable balloon which is placed inside the mesh in a small diameter configuration, and then inflated, thereby expanding the mesh to a larger diameter configuration. The balloon is then deflated for removal, leaving the mesh in its expanded configuration. Both types of mesh constructs may be applied to the present invention.

Figure 23:
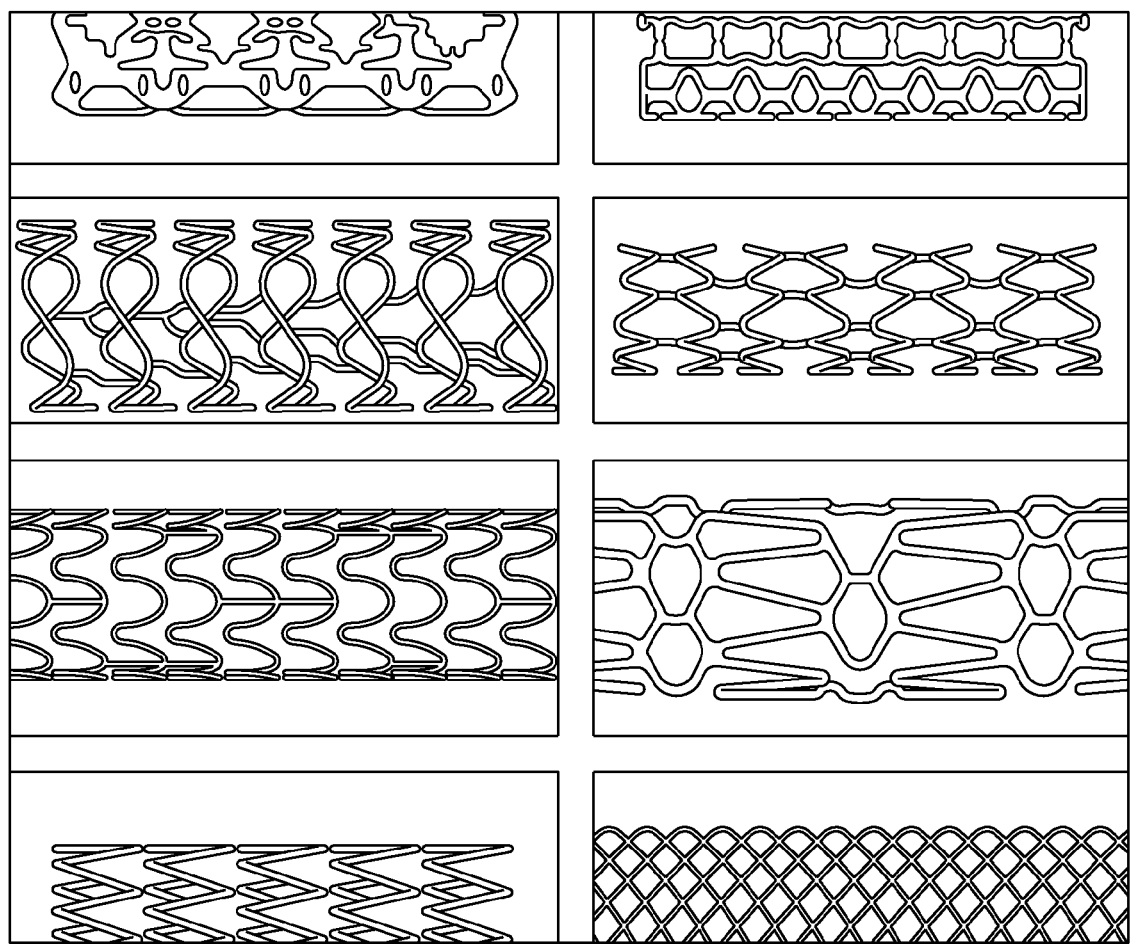
FIG. 23 is a schematic view showing examples of different stent designs.

The expandable mesh intramedullary bone stents can be made from a variety of materials, e.g., stainless steel. The expandable mesh intramedullary bone stents can be made in a variety of configurations such as a coiled spring, a variety of zig-zag patterns (including various stents known as "Z" stents), braided filament, and other collapsible configurations that can have external barbs and/or hooks to help grip the bone tissue. The struts of the intramedullary bone stents can have ribs or teeth to help dig into the bone during axial compression or shortening of stent to help compress the fracture together. See FIG. 23, which shows examples of different stent designs.

One type of expandable stent comprises a cylindrical member having a slit cut along its length, so that the edges along the length can overlap to allow for compression to a reduced size. A further configuration which may be described as a perforated tube which comprises a generally rigid tube with openings cut therein to allow for radial expansion under force of an expansion balloon or by expansion due to heating. The expandable mesh stents can be braided, woven, knitted, formed, molded, machined or made by other methods known in the art. Various mesh designs are disclosed, for example, in U.S. Pat. Nos. 4,512,338, 4,503,569, 4,922,905, 4,733,665, 4,950,227, 5,089,006 and 5,061,275. Other materials, configurations and methods of manufacture in addition to those described above are known.

As used herein, the term "expandable mesh" is meant to include, without limitation, self-expanding and non-self-expanding configurations made of any generally rigid or springy material which, when expanded, have an open network or arrangement which would otherwise allow for tissue in-growth, and would not otherwise prevent fluid flow through its walls. Several of these prior art mesh stents have been utilized with a polymeric sheath or cover; however, since these sheaths must be stretched to increase in size, they exert a force that resists expansion, which tends to limit the final expanded size of the mesh. Additionally, this resistance may make expansion more problematic. Alternatively, the sheath may be folded or bundled over the mesh when it is compressed, so that no force is exerted upon expansion.

Figure 24:
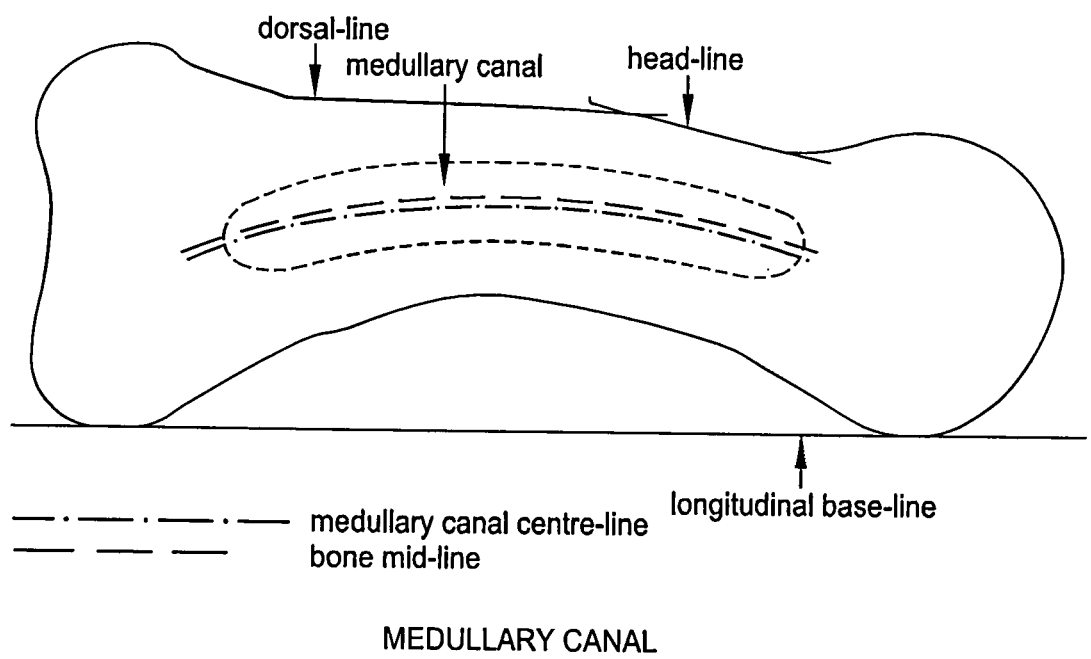
FIGS. 24 and 25 are schematic views showing the intramedullary canal of phalangeal bones.
Figure 25:
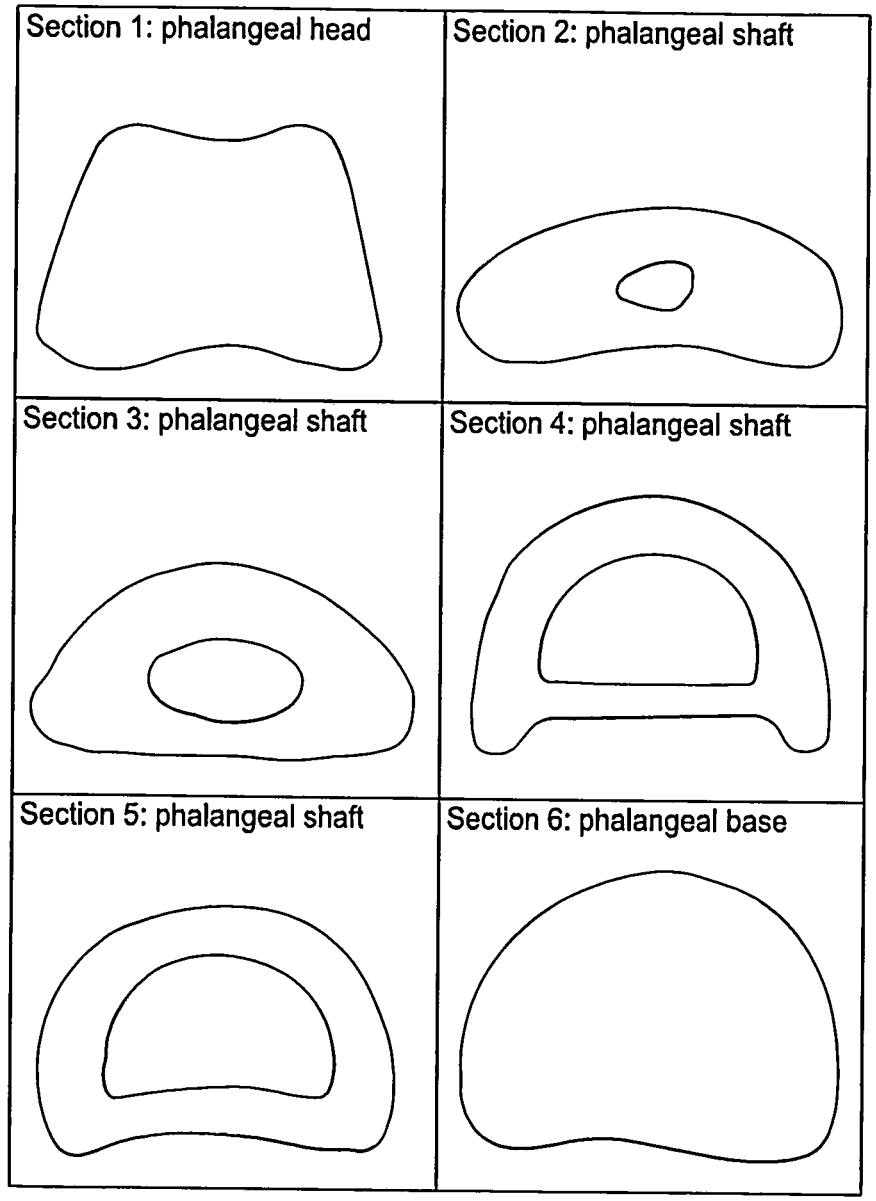

Shape Memory Alloy (SMA) Stents Conform To Different Shapes Of Intramedullary Canals: The proximal and middle phalanges from 83 PIPJs were analyzed set in clear plastic, sectioned in the transverse plane, and measured (Ash and Unsworth 1997). The medullary canals were marked on the sagittal and frontal planes and shadowgraphs of the intact bones analyzed. It was found that the phalangeal shaft bone was thicker laterally than dorsally and palmarly, and thicker dorsally than palmarly for the proximal and middle phalanges throughout the length the hand and wrist. The shape and size of the transverse cross-section of the medullary canal changed throughout the length of the shaft. The centerline of the medullary canal coincided with the midline of the bone in the frontal plane and was approximately a straight line along the length of the canal. In the sagittal plane it was slightly palmar to the midline, and the angle between the centerline and the baseline of the bone changed along the length of the canal. See FIG. 24, which shows the medullary canal of a bone in side view, and FIG. 25, which shows transverse cross-section of phalangeal bones.

The problem with using a machined round pin and/or nail to stabilize the fracture is that the round and straight pin or nail will not conform evenly to the bend and change of bore shape in the medullary canal. Significantly, the flexible SMA intramedullary bone stent of the present invention will conform to the varying geometries of the intramedullary canal. The flexible SMA intramedullary bone stent will radially expand until a certain pressure stops the expansion, which allows the intramedullary bone stent to conform to the specific geometry of the intramedullary canal in terms of straightness and roundness. Also, if the phalangeal shaft bone is thicker in one area vs. the other area, the SMA intramedullary bone stent can be designed to expand more in the thicker section vs. the thinner bone section to allow for uniform strain on the bone tissue.

Figure 26:
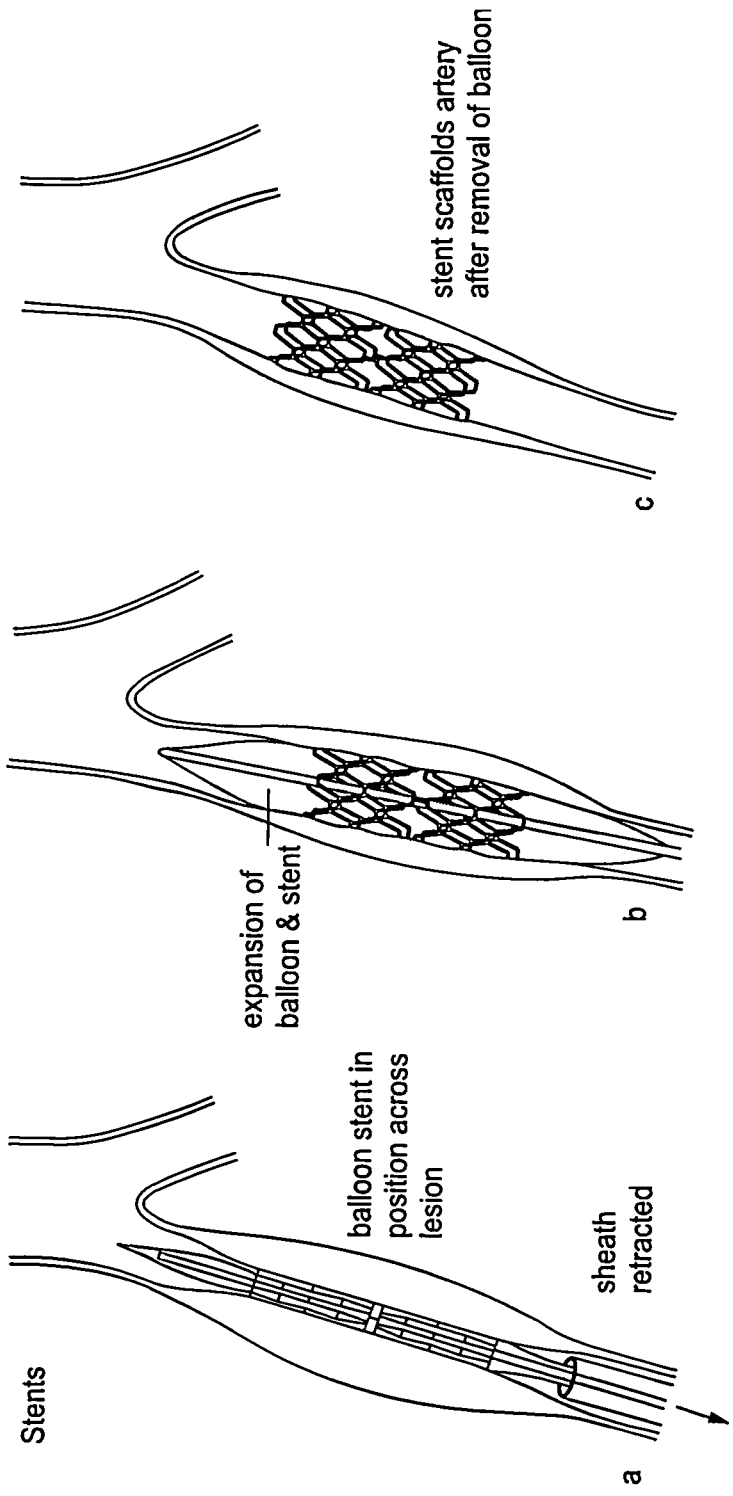
FIG. 26 is a schematic view showing the radial expansion of an intravascular stent.

ZW Stent—Radial Expansion And Axial Compression: Today many intravascular stents are introduced while held inside a polymer sheath. When the sheath is retracted, the intravascular stents expand. If the intravascular stent is Nitinol, it expands superelastically. If the intravascular stent is stainless steel it is expanded with a balloon. Either way, when the sheath is pulled away, the intravascular stent radially expands against the artery. As the sheath is incrementally removed, the expanding intravascular stent applies pressure to the artery. This pressure helps to hold the intravascular stent in place while the sheath is further pulled away, which leaves the more radially expanded exposed stent behind. See the images a, b, c in FIG. 26.

Figure 27:
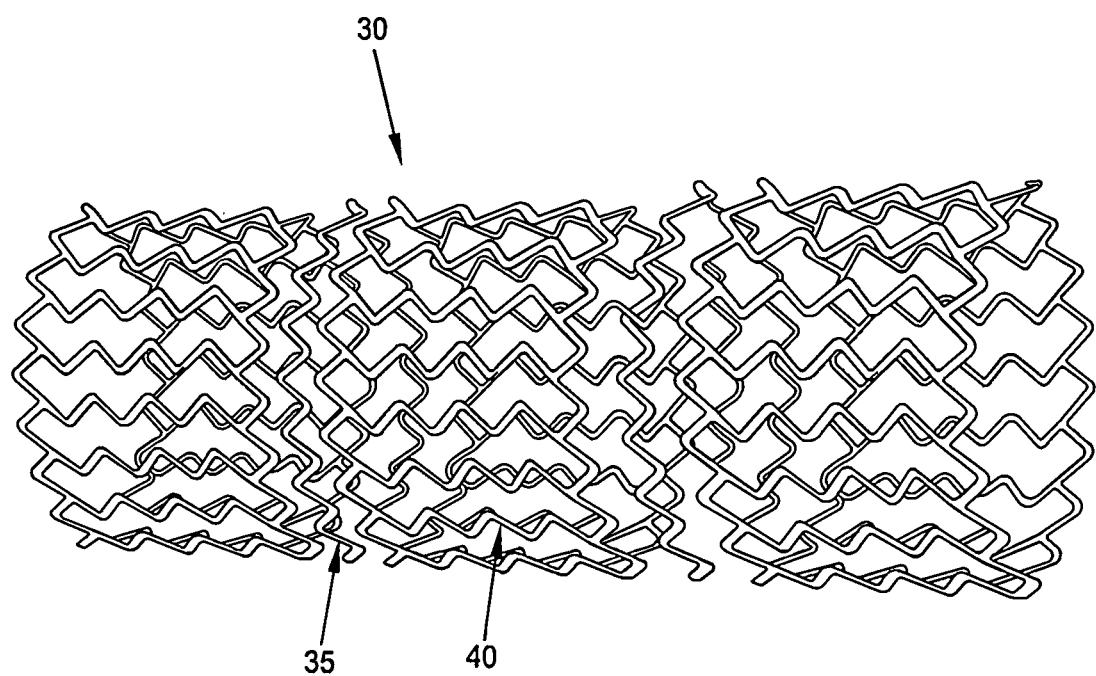
FIG. 27 is a schematic view showing a novel ZW intramedullary bone stent formed in accordance with the present invention.

In accordance with one preferred form of the present invention, an intramedullary bone stent can be engineered to incrementally expand radially when the sheath is removed and then pull in compression. For example, and looking now at FIG. 27, there is shown an intramedullary bone stent 30 which has the conventional "Z" struts 35 that expand radially and, adjacent to the "Z" struts 35, there can be "W" struts 40 which are normal to the "Z"s. The Z struts 35 radially expand and the W struts 40 pull in compression. So, in addition to the traditional stent foreshortening effect which can be used to compress a fracture, the design of the intramedullary bone stent can be further enhanced so as to increase both radial expansion and longitudinal foreshortening.

If desired, the intramedullary bone stent designs can have angular zigzags to help with torsional stability. So, the intramedullary bone stent could have Z struts, W struts, and/or off center line zigzags to improve torsional stability.

Figure 28:
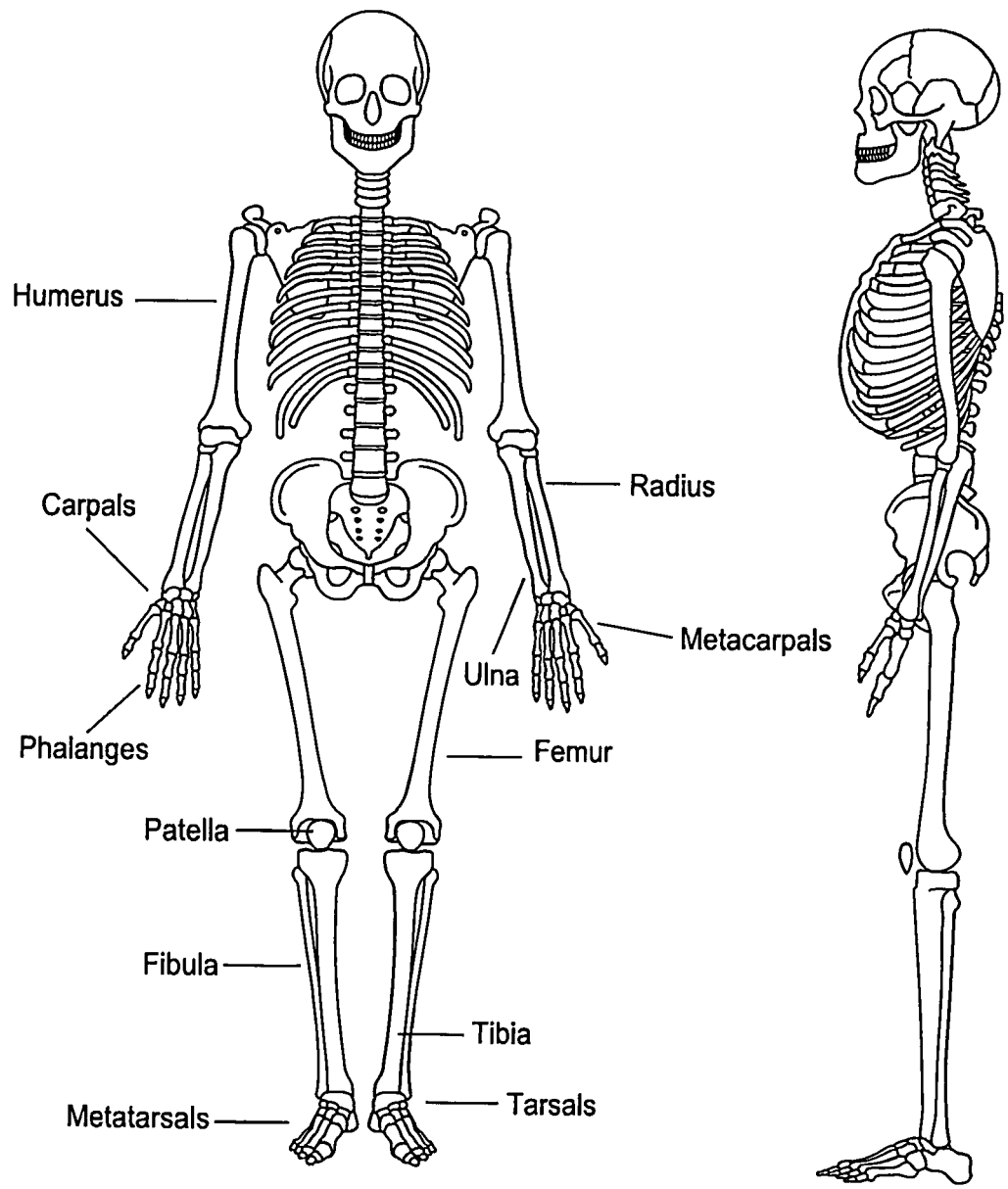
FIG. 28 is a schematic view showing various bones where an intramedullary bone stent may be efficacious for fracture fixation.

Bone stents can be used in the Phalanges, Metacarpals, Carpals, Metatarsals, Tarsals, Humerus, Radius, Ulna, Femur, Tibia and Fibula, among other bones. See FIG. 28, which shows various bones where bone stents may be efficacious for fracture fixation.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for providing stabilization and compression of a bone fracture, the method comprising:
providing an intramedullary prosthesis sized for insertion into the intramedullary canal of a bone, the intramedullary prosthesis consisting of a metallic mesh structure having a round cannulated mesh body terminating in a distal end and a proximal end, and at least two barbs projecting from the round cannulated mesh body;
positioning the intramedullary prosthesis within the intramedullary canal of the bone so that the round cannulated mesh body spans the bone fracture, with at least one of the at least two barbs being disposed on one side of the bone fracture and at least one of the at least two barbs being disposed on the other side of the bone fracture; and
radially expanding and longitudinally contracting the round cannulated mesh body so that the at least two barbs grip the side wall of the intramedullary canal on either side of the bone fracture and pull the bone segments on either side of the bone fracture together, whereby to provide stabilization and compression of the bone fracture.

2. A method according to claim 1 wherein the intramedullary prosthesis comprises a porous structure.

3. A method according to claim 2 wherein the porous structure comprises a stent.

4. A method according to claim 3 wherein the stent comprises Z struts.

5. A method according to claim 3 wherein the stent comprises W struts.

6. A method according to claim 3 wherein the stent comprises Z struts and W struts.

7. A method according to claim 1 wherein the intramedullary prosthesis is self-expanding.

8. A method according to claim 7 wherein the intramedullary prosthesis comprises a shape memory alloy.

9. A method according to claim 8 wherein the shape memory alloy comprises Nitinol.

10. A method according to claim 1 wherein, when the intramedullary prosthesis is in a radially expanded and longitudinally contracted state, the intramedullary prosthesis applies hoop stress radially to the side wall of the intramedullary canal and applies compressive force longitudinally to the side wall of the intramedullary canal so as to close the gap across the bone fracture.

11. A method according to claim 10 wherein the hoop stress is generated by the radial expansion of the intramedullary prosthesis and the compressive force is generated by the foreshortening of the intramedullary prosthesis.

12. A method according to claim 1 wherein the intramedullary prosthesis has a modulus of elasticity which is similar to that of bone.

13. A method according to claim 1 wherein the intramedullary prosthesis has a modulus of elasticity within the range of 1-15 GPa.

14. A method according to claim 1 wherein the intramedullary prosthesis is configured to accommodate bone in-growth.

15. A method according to claim 1 wherein the intramedullary prosthesis is spring-like and oscillates and vibrates so as to cause mechanical loading and catalyze fracture healing.

16. A method according to claim 1 wherein the intramedullary prosthesis is non-self-expanding.

17. A method according to claim 16 wherein the intramedullary prosthesis comprises stainless steel.

18. A method according to claim 1 wherein the intramedullary prosthesis is radially expanded and longitudinally contracted via superelasticity.

19. A method according to claim 1 wherein the intramedullary prosthesis is radially expanded and longitudinally contracted via temperature transition.

20. A method according to claim 1 wherein the intramedullary prosthesis is radially expanded and longitudinally contracted via an expanding balloon.

21. A method for providing stabilization and compression across a dividing line between two bone segments, the method comprising:
providing an intramedullary prosthesis sized for insertion into the intramedullary canal of a bone, the intramedullary prosthesis consisting of a metallic mesh structure having a round elongated mesh body having an axial bore formed therein, and at least two barbs projecting from the round elongated mesh body;
positioning the intramedullary prosthesis within the intramedullary canal of the bone so that the round elongated mesh body spans the dividing line, with at least one of the at least two barbs being disposed on one side of the dividing line and at least one of the at least two barbs being disposed on the other side of the dividing line; and
radially expanding and longitudinally contracting the round elongated mesh body so that the at least two barbs grip the side wall of the intramedullary canal on either side of the dividing line and pull the bone segments on either side of the dividing line together, whereby to provide stabilization and compression across the dividing line.

* * * * *